(12) United States Patent
Dorogusker et al.

(10) Patent No.: US 8,364,389 B2
(45) Date of Patent: Jan. 29, 2013

(54) SYSTEMS AND METHODS FOR INTEGRATING A PORTABLE ELECTRONIC DEVICE WITH A BICYCLE

(75) Inventors: Jesse L. Dorogusker, Los Altos, CA (US); Anthony Fadell, Portola Valley, CA (US); Andrew Hodge, Palo Alto, CA (US); Allen P. Haughay, Jr., San Jose, CA (US); Scott Krueger, San Francisco, CA (US); James Eric Mason, Campbell, CA (US); Donald J. Novotney, San Jose, CA (US); Emily Clark Schubert, San Jose, CA (US); Policarpo Wood, Cupertino, CA (US); Timothy Johnson, San Jose, CA (US)

(73) Assignee: Apple Inc., Cupertino, CA (US)

( * ) Notice: Subject to any disclaimer, the term of this patent is extended or adjusted under 35 U.S.C. 154(b) by 614 days.

(21) Appl. No.: 12/364,103

(22) Filed: Feb. 2, 2009

(65) Prior Publication Data

US 2010/0198453 A1 Aug. 5, 2010

(51) Int. Cl.
*G06G 7/78* (2006.01)
(52) U.S. Cl. ........ 701/300; 701/410; 701/422; 701/428; 701/431; 340/427; 702/182
(58) Field of Classification Search ............ 701/33, 701/208, 213, 200, 207, 300, 410, 422, 428, 701/431; 340/427, 426.24, 432; 280/287; 482/8; 702/182, 142, 150, 176, 96
See application file for complete search history.

(56) References Cited

U.S. PATENT DOCUMENTS

| | | | |
|---|---|---|---|
| 5,335,188 A | 8/1994 | Brisson | |
| 5,471,405 A | 11/1995 | Marsh | |
| 5,547,439 A * | 8/1996 | Rawls et al. | 482/5 |
| 6,013,007 A | 1/2000 | Root et al. | |
| 6,032,108 A | 2/2000 | Seiple et al. | |
| 6,135,951 A | 10/2000 | Richardson et al. | |
| 6,357,147 B1 | 3/2002 | Darley et al. | |
| 6,463,385 B1 | 10/2002 | Fry | |
| 6,539,336 B1 | 3/2003 | Vock et al. | |
| 6,560,903 B1 | 5/2003 | Darley | |
| 6,582,342 B2 | 6/2003 | Kaufman | |
| 6,619,835 B2 | 9/2003 | Kita | |
| 6,716,139 B1 | 4/2004 | Hosseinzadeh-Dolkhani et al. | |
| 6,790,178 B1 | 9/2004 | Mault et al. | |
| 6,793,607 B2 | 9/2004 | Neil | |
| 6,898,550 B1 | 5/2005 | Blackadar et al. | |
| 7,030,735 B2 | 4/2006 | Chen | |
| 7,062,225 B2 | 6/2006 | White | |
| 7,171,331 B2 | 1/2007 | Vock et al. | |
| 7,174,227 B2 | 2/2007 | Kobayashi et al. | |

(Continued)

FOREIGN PATENT DOCUMENTS

WO 02/093272 11/2002
WO 2010/092356 8/2010

*Primary Examiner* — Paul N Dickson
*Assistant Examiner* — Karen Beck
(74) *Attorney, Agent, or Firm* — Fletcher Yoder PC

(57) ABSTRACT

Systems and methods are providing for interfacing an electronic device with a bicycle system. The electronic device can receive the output from sensors coupled to the bicycle and generate riding characteristics for display to the user. The electronic device can in addition receive communications from other electronic devices and provide the communications to the user. In some embodiments, the electronic device can be paired with the devices of one or more other cyclists so that the cyclists can share riding characteristics and other information. This can allow the cyclists to ride as a team and better assist each other.

20 Claims, 9 Drawing Sheets

U.S. PATENT DOCUMENTS

| | | |
|---|---|---|
| 7,200,517 B2 | 4/2007 | Darley et al. |
| 7,251,454 B2 | 7/2007 | White |
| 7,254,516 B2 | 8/2007 | Case, Jr. et al. |
| 7,278,966 B2 | 10/2007 | Hjelt et al. |
| 7,292,867 B2 | 11/2007 | Werner et al. |
| 7,454,002 B1 | 11/2008 | Gardner et al. |
| 7,519,327 B2 | 4/2009 | White |
| 7,618,345 B2 | 11/2009 | Corbalis et al. |
| 7,670,263 B2 | 3/2010 | Ellis et al. |
| 2002/0077784 A1 | 6/2002 | Vock et al. |
| 2003/0097878 A1 | 5/2003 | Farringdon et al. |
| 2004/0102931 A1* | 5/2004 | Ellis et al. .................. 702/188 |
| 2005/0172311 A1 | 8/2005 | Hjelt et al. |
| 2006/0026521 A1 | 2/2006 | Hotelling et al. |
| 2006/0026535 A1 | 2/2006 | Hotelling et al. |
| 2007/0021269 A1 | 1/2007 | Shum |
| 2007/0149364 A1* | 6/2007 | Blau et al. ................... 482/57 |
| 2008/0015089 A1 | 1/2008 | Hurwitz et al. |
| 2009/0150178 A1* | 6/2009 | Sutton et al. ................... 705/2 |
| 2010/0198453 A1* | 8/2010 | Dorogusker et al. ........... 701/33 |
| 2011/0266770 A1* | 11/2011 | Beraka ........................ 280/287 |
| 2012/0016627 A1* | 1/2012 | Nagura ........................ 702/150 |

* cited by examiner

SYSTEMS AND METHODS FOR INTEGRATING A PORTABLE ELECTRONIC DEVICE WITH A BICYCLE

BACKGROUND OF THE INVENTION

This is directed to systems and methods for integrating an electronic device, such as an iPod or iPhone, available from Apple Inc. of Cupertino, Calif., with a bicycle in accordance with one embodiment of the invention.

Many bicyclists desire accessing different information as they ride, such as speed, position, heart rate, power or other information related to components of the bicycle. To provide such information to the cyclist during the ride, a bicycle computer can be coupled to the bicycle, for example on handlebars. The bicycle computer can be connected, using wires or wirelessly, to one or more sensors embedded within the bicycle or in bicycle components. The bicycle computer can receive sensor information and display metrics related to the sensor information on a display for the user. The displayed information can be updated at any suitable interval, for example determined based on power considerations, sensor refresh rates, user requests for particular information, or any other suitable interval.

Bicycle computers, however, are typically expensive components that would not be purchased by casual or semi-serious bicyclists. Many bicycle computers require extensive set-up to connect the bicycle computer to various sensors embedded on the bicycle, for example by requiring a complex wireless pairing procedure or by connecting several wires to the computer. In addition, many bicycle computers only provide information for the bicycle with which the computer is coupled. The bicycle computer can not share information related to the bicycle with which it is coupled with other computers, or can alternatively only provide information related to a ride once the ride is completed and the computer is connected to a host device (e.g., a desktop or laptop computer) that sends the information to a remote server for processing and display.

SUMMARY OF THE INVENTION

This is directed to an electronic device for use with a bicycle system, for example to share information with other cyclists riding in a group.

In some embodiments, a system for communicating riding characteristics among a plurality of bicycles can be provided. The system can include a first electronic device coupled to a first bicycle. The first electronic device can determine riding characteristics, other than location, of the first bicycle. The system can also include a second electronic device coupled to a second bicycle. The second electronic device can be operative to determine at least one riding characteristic of the second bicycle, receive in real-time from the first electronic device the determined riding characteristics of the first bicycle, and provide the determined and received riding characteristics to a display associated with the second electronic device.

In some embodiments, an electronic device for providing cycling information to the users of several bicycles riding in a group can be provided. The electronic device can be associated with a first bicycle, and include control circuitry operative to detect several electronic devices associated with the several bicycles. The control circuitry can be operative to determine at least one riding characteristic of the first bicycle, and receive, in real-time from each of the detected several electronic devices, at least one riding characteristic of each of the plurality of bicycles. Riding characteristic can include at least one of speed, distance, time, altitude, elevation, incline, decline, heart rate, power, derailleur setting, cadence, wind speed, path completed, expected future path, heart rate, power, and pace.

In some embodiments, a sensor for use with an electronic device can be provided. The sensor can be coupled to a bicycle and include communications circuitry operative to pair with at least one authorized electronic device. The sensor can also include control circuitry operative to monitor the movement of at least one bicycle component, determine, from the monitored movement, that the bicycle is in use, detect that the communications circuitry has not received a communication from the at least one authorized electronic device, and generate an alert indicating that the bicycle is being used without authorization. The control circuitry can then direct the communications circuitry to broadcast the alert, for example to a remote server.

BRIEF DESCRIPTION OF THE DRAWINGS

The above and other features of the present invention, its nature and various advantages will be more apparent upon consideration of the following detailed description, taken in conjunction with the accompanying drawings in which.

DETAILED DESCRIPTION

Figure 1:
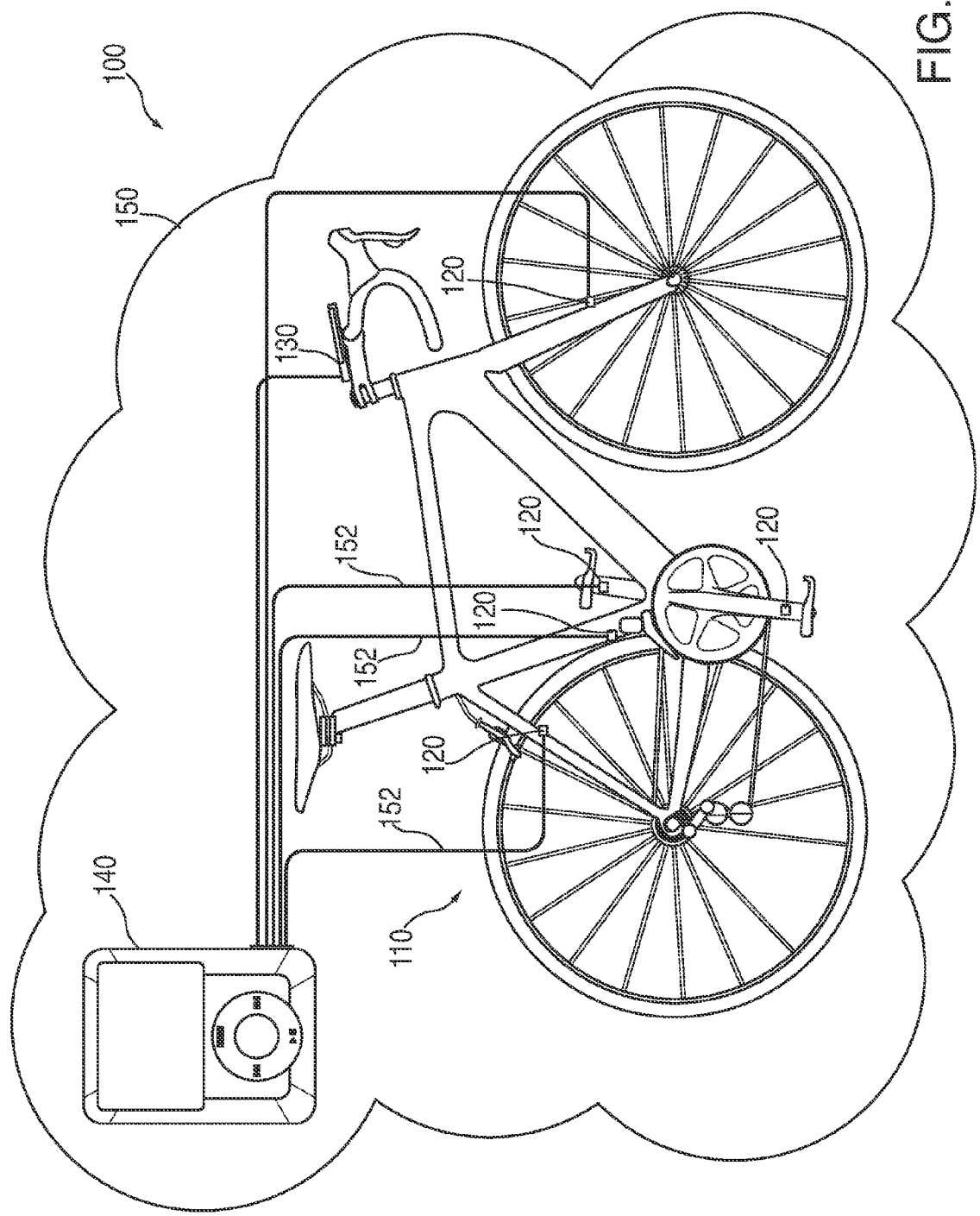
FIG. 1 is a schematic view of an illustrative system for providing riding characteristics to a user of a bicycle in accordance with one embodiment of the invention.

This is related to an electronic device for use with a bicycle or in a cycling environment to provide feedback to cyclists regarding their performance or the performance of other cyclists with whom they are riding. In some embodiments, this can be applied to users of other types of vehicles (e.g., motorcycles, automobiles, or trucks) or other modes of transportation (e.g., walking, running, horseback riding, or transportation using any other animal). Although many features described below can be in the context of a bicycle or cycling embodiment, it will be understood that the features or descriptions can be applied to any suitable vehicle or mode of transportation.

In some embodiments, an electronic device that can be coupled to a bicycle or other vehicle can be provided. The electronic device can include one or more instances of communications circuitry for sending or receiving communications, positioning circuitry for determining the current position or location of the electronic device or of a component coupled to the electronic device (e.g., via the communications circuitry), and a processor or control circuitry for processing communications information, location data, and other data received or generated by the electronic device. In some embodiments, the communications circuitry can be operative to receive information from one or more sensors embedded in or coupled to the bicycle or vehicle. For example, the electronic device can receive information from a strain gage, cadence sensor, speedometer, accelerometer, or switch coupled to a bicycle. The received information can include raw data output by the sensors, or processed data descriptive of one or more riding characteristics or movement characteristics of the bicycle, vehicle, or mode of transportation. In some embodiments, the riding characteristics determined and provided to the user can be selected based on the type of bicycle or vehicle being used, the course or type of path being ridden, or metrics known to be of interest to the user (e.g., a mountain bike and a road bike can be associated with different riding characteristics).

The electronic device can be operative to provide information to the user using any suitable approach. In some embodiments, a display can receive information from the electronic device and provide received information for display to the user. The displayed information can be changed or updated using any suitable approach, including for example in response to receiving a user input on the electronic device (e.g., the electronic device provides new information for display or directs the display to display previously provided information in response to detecting a button press), in response to receiving a user input on the display (e.g., the display sends a request for new information to the electronic device or displays previously received information), or automatically (e.g., displayed information is automatically refreshed at a known or pre-determined rate). The electronic device can provide information to the display at any suitable interval, including for example at regular intervals, pre-determined intervals, when a particular amount or type of information is received or processed by the electronic device (e.g., a transmission buffer is full, or a riding characteristic of interest to the user changes), in response to receiving a user request (e.g., the user provides an input requesting that particular information be displayed), or any other suitable interval. The display can be located at any suitable position, including for example on or as part of the bicycle (e.g., a display placed on the handlebars, or embedded within the handlebars), in an enclosure or case attached to the vehicle or to the user (e.g., in an arm strap), or at any other suitable position.

In some embodiments, the electronic device can display information other than the status of one or more sensors coupled to the user's bicycle or vehicle. The other information can come from any suitable source, including for example one or more dedicated servers, the Internet, or any other suitable source. Any suitable information can be displayed, including for example maps or other location based information of interest to the user. In particular, the electronic device can provide courses for the user to ride, or local attractions or sights to see. The electronic device can use positioning circuitry to identify courses or attractions that begin at or near the user's current position, or that are within a given distance of a user's expected future position (e.g., if the electronic device can predict which course a user will take, the electronic device can identify attractions or alternate courses in the vicinity of locations along the user's expected course).

As another example, the electronic device can provide comparison profiles for display to the user. A comparison profile can include one or more target sensor outputs or riding characteristics for a particular ride or course by a particular cyclist. The sensor outputs or riding characteristics can change with time or with a particular position on the course, such that a user can view the evolution of the comparison profile during the ride (e.g., the speed of the comparison profile at different areas of the course, or the gear or derailleur ratios used on particular hills or flat areas). Comparison profiles can be generated using any suitable approach, including for example by recording a cyclist's performance during a ride, combining a cyclist's past performances (e.g., a user history comparison profile), based on an average of known performances by cyclists having a particular skill level, or based on a generated sample or generic performance to be expected by a cyclist of a particular skill level (e.g., as determined by computer simulations). As a cyclist rides, the electronic device can provide displays comparing one or more metrics (e.g., sensor outputs or riding characteristics) of the cyclist's performance with corresponding metrics of the comparison profile. The cyclist can then monitor his performance relative the comparison profile to detect improvements in performance (e.g., when the comparison profile is based on a prior ride by the same cyclist), define goals or targets (e.g., match one or more metrics of a more advanced comparison profile), monitor his health (e.g., notice when power output abnormally decreases), or for any other suitable purpose.

In some embodiments, the electronic device can display information related to or received from other cyclists. The user can select the other cyclists of interest based on any suitable criteria, including for example cyclists riding with the user (e.g., a group of cyclists), a cycling team, cyclists participating in a race or other event (e.g., a charity event), other cyclists in the vicinity, or any other suitable criteria. To provide information to the electronic device, some or all of the cyclists in the group can have electronic devices operative to perform communications operations. Instead or in addition, some or all of the other bicycles can include one or more sensors operative to provide information to the user's electronic device or to electronic devices of the other cyclists. In some embodiments, the electronic device can perform communications operations with the electronic devices of one or more cyclists. For example, the electronic device can transmit a voice, text or video message to one or more other devices, or receive a text, voice or video message from one or more of the other devices.

The electronic device can provide received communications to the user using any suitable approach. For example, text and video communications, or any other communication that the user can see can be provided to the user's display (e.g., on the bicycle). As another example, audio communications can be provided using a headset or headphones connected to one of the display and the electronic device, or using one or more speakers of the display or electronic device. As still another example, both a display and an audio source can be used in combination to provide video conferencing capabilities. In some embodiments, the electronic device can initially provide one or more notifications or metadata associated with a received communication to allow the user to elect whether or not to view or access the communication (e.g., display a notification indicating that a new text message was received from a particular cyclist). The displayed notifications or metadata can be provided for different types of communications, including for example non-visual communications (e.g., identify the cyclist desiring to perform a voice communication). A user can generate a communication using any suitable approach, including for example using voice-activated instructions (e.g., provided using a microphone), selecting pre-existing or pre-generated messages, or entering new messages using an input mechanism of the display or electronic device.

In some embodiments, the electronic device can receive and display any suitable type of information received from other cyclists, including for example riding characteristics or sensor outputs received from sensors or electronic devices associated with the other cyclists. Using the received metrics, the electronic device can provide riding recommendations for the user to catch up to, ride with, or ride faster than one or more cyclists within the group. For example, the electronic device can direct the user to ride at a particular speed, or at a particular cadence and gear ratio based on the metrics associated with one or more other riders. In some embodiments, the electronic device can indicate a path for the user to ride to reach a destination ahead of, behind, or at the same time as other cyclists, or to meet other cyclists at a particular time or in a particular distance. The electronic device can also, based on the riding characteristics of each of the cyclists (e.g., power generated and calories burned), recommend that a particular cyclist ride in front so that other cyclists (e.g., cyclists that are fatigued or a team leader) can draft the particular cyclist to conserve power.

To secure a bicycle having sensors operative to communicate with an electronic device, a pairing system can be used to determine whether a user having an unauthorized electronic device is using the bicycle. In particular, when an authorized electronic device is first used, the user can pair the electronic device with the one or more sensors. When an electronic device is subsequently brought in the vicinity of the one or more sensors, the sensors can determine whether the electronic device has been paired with the sensors. For example, each electronic device can automatically identify itself to the sensors coupled to the bicycle. Alternatively, the sensors can automatically detect an electronic device brought in the vicinity of the bicycle. If the sensors detect that the bicycle is being ridden (e.g., based on the sensor output) while only an unpaired or unauthorized electronic device remains in the vicinity of the sensors (e.g., the cyclist using the bicycle is carrying the unauthorized electronic device), the sensors can broadcast an alert indicating that the bicycle can be stolen and providing time and location or position information. The unauthorized electronic device, or other electronic devices in the vicinity of the bicycle can then transmit the alert to a remote server accessible to the owner of the bicycle.

In an alternative embodiment, the sensors can expect a paired electronic device to be present each time the bicycle is ridden. If the sensors determine that the bicycle is in movement, but that no authorized electronic device is in communication with the sensors, the sensors can similarly broadcast an alert indicating that the bicycle can be stolen. Other electronic devices can then re-transmit the alert to a remote server. This approach can allow an alert to be broadcast even when an unauthorized user of the bicycle does not have an electronic device operative to communicate with the sensors.

FIG. 1 is a schematic view of an illustrative system for providing riding characteristics to a user of a bicycle in accordance with one embodiment of the invention. System 100 can include bicycle 110, sensors 120, display 130, and electronic device 140. Sensors 120, display 130 and electronic device 140 can communicate via communications network 150. Bicycle 110 can include any suitable type of bicycle, including for example a road bicycle, racing bicycle, mountain bicycle, touring bicycle, BMX bicycle, electric bicycle, or any other suitable type of bicycle. As discussed above, it will be understood that in some embodiments, other vehicles or modes of transportation can be used instead of bicycle 110. Bicycle 110 can include one or more sensors 120 for determining the status of different bicycle components, or for monitoring the manner or environment in which the bicycle is operated (e.g., by monitoring characteristics of the user of bicycle 110). Sensors 120 can include sensors for detecting any suitable metric related to the use of bicycle 110, including for example speed, pace, acceleration, distance, time, incline, decline, altitude, torque, power generated, cadence, gear and derailleur settings, heart rate, calories burned, weather, and temperature. Any suitable type of sensor can be used to determine one or more of these metrics, including for example a Hall effect sensor, a magnetic sensor, a strain gauge, a photo-electric sensor, an audio pick-up, a heart rate monitor (e.g., using a piezoelectric strip), an accelerometer, positioning circuitry (e.g., Global Positioning System, GPS circuitry), or any other suitable sensor.

Display 130 can include any suitable type of display. In some embodiments, display 130 can include a removable display that can be coupled to bicycle 110, for example on the handlebars. As another example, display 130 could be placed in a pouch or holder and coupled to the user's arm or wrist for easy access. In some embodiments, display 130 can instead or in addition be embedded in bicycle 110. For example, the display can be permanently coupled to the bicycle handlebars (e.g., a liquid crystal display embedded in an opening in the handlebars). As another example, the display can be provided in the handlebars using micro perforations through which light can be selectively emitted to provide information to the user. In some embodiments, display 130 can include an input mechanism (e.g., a button) for controlling the information displayed, or for controlling communications sent to or received from sensors 120 and electronic device 140.

In some embodiments, display 130 can include a screen on which content can be provided. The screen can include, for example, a liquid crystal display (LCD), light emitting diode (LED) display, organic light-emitting diode (OLED) display, surface-conduction electron-emitter display (SED), carbon nanotubes, nanocrystal displays, or any other suitable type of display that can be incorporated in or coupled to bicycle 110. Alternatively, display 130 can include a movable display or a projecting system for providing a display of content on a surface remote from bicycle 110, such as a video projector, head-up display, or three-dimensional (e.g., holographic) display. In some embodiments, display 130 can include circuitry including a coder/decoder (Codec) to convert digital media data into analog signals.

Electronic device 140 can include any suitable type of electronic device operative to communicate with sensors 120 and display 130. For example, electronic device 140 can include a media player such as an iPod® available by Apple Inc., of Cupertino, Calif., a cellular telephone, a personal e-mail or messaging device (e.g., a Blackberry® or a Sidekick®), an iPhone® available from Apple Inc., pocket-sized personal computers, personal digital assistants (PDAs), a desktop computer, a laptop computer, a cyclocomputer, a music recorder, a video recorder, a camera, radios, medical equipment, domestic appliances, transportation vehicle instruments, calculators, and any other portable electronic device capable of being carried in the vicinity of bicycle 110 (or any other suitable vehicle). In some cases, electronic device 140 can perform a single function (e.g., a device dedicated to playing music) and in other cases, electronic device 140 can perform multiple functions (e.g., a device that plays music, displays video, stores pictures, and receives and transmits telephone calls).

Communications network 150 can be created by any suitable circuitry, device, system or combination of these (e.g., a wireless communications infrastructure including communications towers and telecommunications servers). Communications network 150 can be capable of providing wireless communications using any suitable short-range or long-range communications protocol. In some embodiments, communications network 150 can support, for example, Wi-Fi (e.g., a 802.11 protocol), Ethernet, Bluetooth®, radio frequency systems, cellular networks (e.g., GSM, AMPS, GPRS, CDMA, EV-DO, EDGE, 3GSM, DECT, IS-136/TDMA, iDen, LTE or any other suitable cellular network or protocol), infrared, TCP/IP (e.g., any of the protocols used in each of the TCP/IP layers), HTTP, BitTorrent, FTP, RTP, RTSP, SSH, Voice over IP (VOIP), any other communications protocol, or any combination thereof Wi-Fi (e.g., a 802.11 protocol), Bluetooth (registered trademark), radio frequency systems (e.g., 900 MHz, 2.4 GHz, and 5.6 GHz communication systems), infrared, other relatively localized wireless communication protocol, or any combination thereof. Sensors 120, display 130 and electronic device 140 can wirelessly communicate over local wireless communication paths such as paths 152. In some embodiments, communications paths 152 can include wired paths, or combinations of wired and wireless paths.

Figure 2:
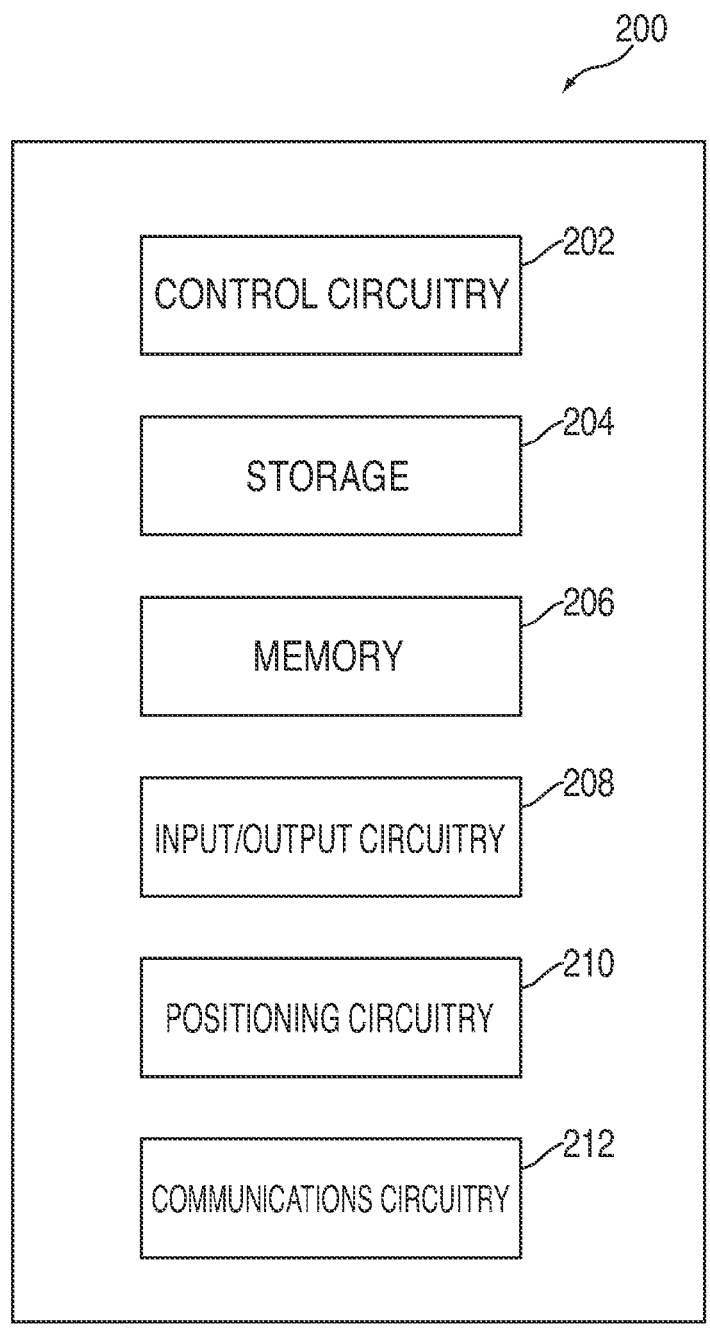
FIG. 2 is a schematic view of an illustrative electronic device for receiving the output of one or more sensors in accordance with one embodiment of the invention.

FIG. 2 is a schematic view of an illustrative electronic device for receiving the output of one or more sensors in accordance with one embodiment of the invention. Electronic device 200 can include control circuitry 202, storage 204, memory 206, input/output circuitry 208, positioning circuitry 210, and communications circuitry 212. In some embodiments, one or more of electronic device components 200 can be combined or omitted (e.g., combine storage 204 and memory 206). In some embodiments, electronic device 200 can include other components not combined or included in those shown in FIG. 2 (e.g., motion detection components, a power supply (e.g., a battery or kinetics), a display, bus, or input mechanism), or several instances of the components shown in FIG. 2. For the sake of simplicity, only one of each of the components is shown in FIG. 2.

Control circuitry 202 can include any processing circuitry or processor operative to control the operations and performance of electronic device 200. For example, control circuitry 200 can be used to run operating system applications, firmware applications, media playback applications, media editing applications, or any other application. In some embodiments, the control circuitry can drive a display and process inputs received from a user interface.

Storage 204 can include, for example, one or more storage mediums including a hard-drive, solid state drive, flash memory, permanent memory such as ROM, any other suitable type of storage component, or any combination thereof. Storage 204 can store, for example, media data (e.g., music and video files), application data (e.g., for implementing functions on device 200), firmware, user preference information data (e.g., media playback preferences), authentication information (e.g. libraries of data associated with authorized users), lifestyle information data (e.g., food preferences), exercise information data (e.g., information obtained by exercise monitoring equipment), transaction information data (e.g., information such as credit card information), wireless connection information data (e.g., information that can enable electronic device 200 to establish a wireless connection), subscription information data (e.g., information that keeps track of podcasts or television shows or other media a user subscribes to), contact information data (e.g., telephone numbers and email addresses), calendar information data, and any other suitable data or any combination thereof.

Memory 206 can include cache memory, semi-permanent memory such as RAM, and/or one or more different types of memory used for temporarily storing data. In some embodiments, memory 206 can also be used for storing data used to operate electronic device applications, or any other type of data that can be stored in storage 204. In some embodiments, memory 206 and storage 204 can be combined as a single storage medium.

Input/output circuitry 208 can be operative to convert (and encode/decode, if necessary) analog signals and other signals into digital data. In some embodiments, input/output circuitry 208 can also convert digital data into any other type of signal, and vice-versa. For example, input/output circuitry 208 can receive and convert physical contact inputs (e.g., from a multi-touch screen), physical movements (e.g., from a mouse or sensor), analog audio signals (e.g., from a microphone), or any other input. The digital data can be provided to and received from processor 202, storage 204, memory 206, or any other component of electronic device 200. Although input/output circuitry 208 is illustrated in FIG. 2 as a single component of electronic device 200, several instances of input/output circuitry can be included in electronic device 200.

Electronic device 200 can include any suitable mechanism or component for allowing a user to provide inputs to input/output circuitry 208. For example, electronic device 200 can include any suitable input mechanism, such as for example, a button, keypad, dial, a click wheel, or a touch screen. In some embodiments, electronic device 200 can include a capacitive sensing mechanism, or a multi-touch capacitive sensing mechanism. Some sensing mechanisms are described in commonly owned Hotelling et al. U.S. Published Patent Application No. 2006/0026521, filed Jul. 30, 2004, entitled "Gestures for Touch Sensitive Input Device," and Hotelling et al. U.S. Published Patent Application No. 2006/0026535, filed Jan. 28, 2005, entitled "Mode-Based Graphical User Interfaces for Touch Sensitive Input Device," both of which are incorporated herein in their entirety.

In some embodiments, electronic device 200 can include specialized output circuitry associated with output devices such as, for example, one or more audio outputs. The audio output can include one or more speakers (e.g., mono or stereo speakers) built into electronic device 200, or an audio component that is remotely coupled to electronic device 200 (e.g., a headset, headphones or earbuds that can be coupled to communications device with a wire or wirelessly).

In some embodiments, I/O circuitry 208 can include display circuitry (e.g., a screen or projection system) for providing a display visible to the user. For example, the display circuitry can include a screen (e.g., an LCD screen) that is incorporated in electronics device 200. As another example, the display circuitry can include a movable display or a projecting system for providing a display of content on a surface remote from electronic device 200 (e.g., a video projector). In some embodiments, the display circuitry can include a coder/ decoder (Codec) to convert digital media data into analog signals. For example, the display circuitry (or other appropriate circuitry within electronic device 200) can include video Codecs, audio Codecs, or any other suitable type of Codec.

The display circuitry also can include display driver circuitry, circuitry for driving display drivers, or both. The display circuitry can be operative to display content (e.g., media playback information, application screens for applications implemented on the electronic device, information regarding ongoing communications operations, information regarding incoming communications requests, or device operation screens) under the direction of control circuitry 202. Alternatively, the display circuitry can be operative to provide instructions to a remote display (e.g., display 130, FIG. 1).

Positioning circuitry 210 can include any suitable circuitry for determining the current position of electronic device 200, and can be operative to update the current position at any suitable rate, including at relatively high rates to provide an estimation of speed and distance traveled. In some embodiments, positioning circuitry 210 can include a global positioning system ("GPS") receiver for accessing a GPS application function call that returns the geographic coordinates (i.e., the geographic location) of the device. The geographic coordinates can be fundamentally, alternatively, or additionally derived from any suitable trilateration or triangulation technique. For example, the device can determine its location using various measurements (e.g., signal-to-noise ratio ("SNR") or signal strength) of a network signal (e.g., a cellular telephone network signal) associated with the device. For example, a radio frequency ("RF") triangulation detector or sensor integrated with or connected to the electronic device can determine the approximate location of the device. The device's approximate location can be determined based on various measurements of the device's own network signal, such as: (1) the angle of the signal's approach to or from one or more cellular towers, (2) the amount of time for the signal to reach one or more cellular towers or the user's device, (3) the strength of the signal when it reaches one or more towers or the user's device, or any combination of the aforementioned measurements, for example. Other forms of wireless-assisted GPS (sometimes referred to herein as enhanced GPS or A-GPS) can also be used to determine the current position of electronic device 200.

In some embodiments, a device can determine its location based on a wireless network or access point that is in range or a wireless network or access point to which the device is currently connected. For example, because wireless networks have a finite range, a network that is in range of the device can indicate that the device is located in the approximate geographic location of the wireless network. In some embodiments, the device can automatically connect to a wireless network that is in range in order to receive the valid modes of operation for that location.

Communications circuitry 212 can include any suitable communications circuitry operative to connect to a communications network (e.g., communications network 150, FIG. 1) and to transmit communications (e.g., voice or data) from communications device 200 to other devices within the communications network. Communications circuitry 212 can be operative to interface with the communications network using any suitable communications protocol such as, for example, Wi-Fi (e.g., a 802.11 protocol), Bluetooth®, radio frequency systems (e.g., 900 MHz, 2.4 GHz, and 5.6 GHz communication systems), infrared, GSM, GSM plus EDGE, CDMA, quadband, and other cellular protocols, VOIP, or any other suitable protocol.

In some embodiments, communications circuitry 212 can be operative to create a communications network using any suitable communications protocol. For example, communications circuitry 212 can create a short-range communications network using a short-range communications protocol to connect to other devices. For example, communications circuitry 212 can be operative to create a local communications network using the Bluetooth® protocol to couple electronic device 200 with a Bluetooth® headset.

Electronic device 200 can include one more instances of communications circuitry 212 for simultaneously performing several communications operations using different communications networks, although only one is shown in FIG. 2 to avoid overcomplicating the drawing. For example, electronic device 200 can include a first instance of communications circuitry 212 for communicating over a cellular network, and a second instance of communications circuitry 212 for communicating over Wi-Fi or using Bluetooth®. In some embodiments, the same instance of communications circuitry 212 can be operative to provide for communications over several communications networks.

In some embodiments, electronic device 200 can be coupled a host device for data transfers, synching the communications device, software or firmware updates, providing performance information to a remote source (e.g., providing riding characteristics to a remove server) or performing any other suitable operation that can require electronic device 200 to be coupled to a host device. Several electronic devices 200 can be coupled to a single host device using the host device as a server, and instead or in addition electronic device 200 can be coupled to several host devices (e.g., for each of the plurality of the host devices to serve as a backup for data stored in electronic device 200).

In some embodiments, electronic device 200 can include a motion sensing component operative to detect movements of electronic device 200. For example, a motion sensor can be operative to detect a user's movements of electronic device 200. In some embodiments, a motion sensor can include one or more three-axes acceleration motion sensors (e.g., an accelerometer) operative to detect linear acceleration in three directions (i.e., the x or left/right direction, the y or up/down direction, and the z or forward/backward direction). As another example, a motion sensor can include one or more two-axis acceleration motion sensors which can be operative to detect linear acceleration only along each of x or left/right and y or up/down directions (or any other pair of directions). In some embodiments, a motion sensor can include an electrostatic capacitance (capacitance-coupling) accelerometer that is based on silicon micro-machined MEMS (Micro Electro Mechanical Systems) technology, a piezoelectric type accelerometer, a piezoresistance type accelerometer, or any other suitable accelerometer.

In some embodiments, the motion sensor can directly detect rotation, rotational movement, angular displacement, tilt, position, orientation, motion along a non-linear (e.g., arcuate) path, or any other non-linear motions. For example, if the motion sensor is a linear motion sensor, additional processing can be used to indirectly detect some or all of the non-linear motions. For example, by comparing the linear output of the motion sensor with a gravity vector (i.e., a static acceleration), the motion sensor can calculate the tilt of electronic device 200 with respect to the y-axis. In some embodiments, the motion sensor can instead or in addition include one or more gyro-motion sensors or gyroscopes for detecting rotational movement. For example, motion sensor 210 can include a rotating or vibrating element.

In some embodiments, electronic device 200 can include a bus operative to provide a data transfer path for transferring data to, from, or between control processor 202, storage 204, memory 206, input/output circuitry 208, positioning circuitry 210, communications circuitry 212, and any other component included in the electronic device.

As a rider of the bicycle of system 100 (FIG. 1) operates the bicycle, the sensor coupled to the bicycle, as well as sensors of the electronic device can gather information related to the user's performance or ride. For example, the sensors, electronic device, or both can gather information regarding the forces applied by the user on the bicycle, the forces from the environment to which the bicycle is subjected (e.g., acceleration, Coriolis force, temperature, incline, or wind), the location of the bicycle, time and intervals during the ride (e.g., which can be used with position or acceleration data to determine speed), the user's condition (e.g., heart rate) or any other suitable information that can be determined by one or more sensors. The raw sensor data can be processed to generate riding characteristics reflective of the manner in which the user is riding the bicycle. Such riding characteristics can include, for example, acceleration, speed, distance, time or intervals of time between events, altitude or elevation of the bicycle, incline/decline during the ride, wind speed, location, path completed, expected future path power, force applied to particular bicycle components (e.g., pedals), cadence, derailleur setting, heart rate, calories burned, air time, falls, impacts received, jump height or any other characteristic or metric that can be determined from the output of one or more sensors or electronic device components and that can be of use to a cyclist. In some embodiments, riding characteristics can include the raw data provided by one or more sensors (e.g., the rotations per unit of time of the bicycle's wheels).

Any suitable component or combination of components can process sensor data or other data to generate one or more riding characteristics. In some embodiments, data from different sensors can be used to determine the same riding characteristic, but with different levels of accuracy. For example, speed can be determined based on changes in position over time as determined by positioning circuitry (e.g., a GPS system of the electronic device), integrating accelerometer data over a time interval (e.g., an accelerometer as part of a motion sensing component of the electronic device), and based on wheel revolutions as calculated by a magnetic switch coupled to the fork or hub of the bicycle. In some embodiments, the information provided by each sensor or component can be combined to provide a more accurate perspective of a riding characteristic (e.g., a force applied to the bicycle, such as wind speed, can have different values based on the position of each of the sensors detecting the wind).

Data processing of the raw data generated by each of the sensors can take place at any suitable location in the bicycle system. For example, one or more of the sensors, the display, and the electronic device can process raw data. To reduce the cost of the sensors coupled to or embedded in the bicycle, the electronic device can perform a substantial amount of the processing. The sensors can provide data to the electronic device, or other processing entity at any suitable interval, including for example continuously or substantially continuously, at determined intervals (e.g., determined time intervals), based on the amount of information detected or generated by the sensor (e.g., when a buffer is full), in response to detecting a particular event (e.g., detecting an event having a particular magnitude or lasting a particular duration), in response to detecting a connection having a particular strength (e.g., detecting an electronic device within a few feet of the sensors, as it would be if the bicycle user were carrying the electronic device), or any other suitable interval.

Figure 3:
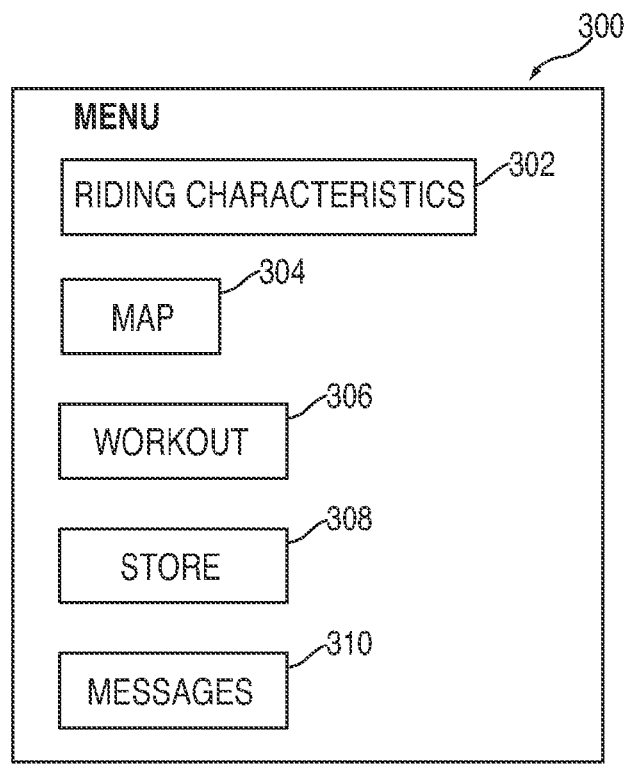
FIG. 3 is a schematic view of an illustrative display provided for controlling the display of information to a user in accordance with one embodiment of the invention.

FIG. 3 is a schematic view of an illustrative display provided for controlling the display of information to a user in accordance with one embodiment of the invention. Display 300 can include any suitable option for controlling the information provided to the user. For example, display 300 can include Riding Characteristics option 302, Map option 304, Workout Option 306, Share option 308, and Messages option 310. In some embodiments, other options can be displayed in addition to or instead of the options shown in display 300.

The user can select a displayed option, or access other options (e.g., by selecting or providing a More instruction) using any suitable approach. In some embodiments, the user can provide an instruction using an input mechanism associated with the display. The input mechanism can be embedded in or coupled to the display (e.g., one or more buttons, switches or a touch screen), or include an input mechanism remote from the display (e.g., a wired or wireless button or switch located on the handlebars near the brakes or shifters, or a touch screen or touch pad embedded in the handlebar grips). In some embodiments, the user can instead or in addition use an input mechanism associated with the electronic device. For example, the input mechanism can include one or more buttons, switches, a touch screen, a scroll wheel, or any other suitable input mechanism included in the electronic device. Because the electronic device can be located in a user's pocket, or in a location away from the user's hands, the electronic device can be associated with a hands-free input mechanism, or a remote input mechanism positioned near the user's hands. For example, the electronic device can receive inputs from voice or other audio commands (e.g., using a microphone coupled to the electronic device), based on the user's movements (e.g., using an accelerometer or other motion sensing component located in the electronic device or placed on the user, for example on the user's head or helmet or on the user's arm), or any other suitable hands-free input mechanism. As another example, the electronic device can receive inputs using a wired or wireless remote controller, for example located near the user's hands (e.g., on the handlebar). The remote controller can include any suitable input mechanism, including for example one or more buttons, switches, touch screens, or any other suitable input mechanism.

The generated riding characteristics can be provided to the user using any suitable approach. In some embodiments, the riding characteristics can be provided as audio to the user. For example, the user can have a headset or earpiece through which audio feedback can be provided. As another example, one or more of the display and electronic device can include a speaker or audio output component for providing audio reflecting riding characteristics. In some embodiments, the riding characteristics can instead or in addition be visually provided to the user. For example, a visual representation of one or more riding characteristics can be provided to the user using any suitable approach, for example automatically or in response to a user request. Subsequent riding characteristics can be provided instead of or in addition to currently or previously provided characteristics (e.g., add or replace displayed information, or repeat previously provided audio feedback before providing the next feedback). The subsequent riding characteristics can be provided automatically, for example as a cycle of riding characteristics, or in response to the user requesting subsequent information (e.g., in response to receiving an input from an input mechanism). In some embodiments, the input mechanism can allow a user to request and access a particular riding characteristic or set of riding characteristics of interest.

In some embodiments, riding characteristics can be provided based on the user's environment or in response to detecting particular events. For example, if a riding characteristic exceeds a particular threshold (e.g., power is too low, or heart rate is too high), the riding characteristic can be provided to the user. As another example, if a riding characteristic reaches a milestone value (e.g., a best time, longest or fastest ride, steepest climb or descent), the riding characteristic can be automatically provided to the user. In some embodiments, a default riding characteristic can be provided to the user unless an event (e.g., an event or a user input) is detected. The default riding characteristic can include any suitable characteristic or set of characteristics, including for example the characteristic of most interest to the user for the particular ride (e.g., time in a time trial).

Figure 4:
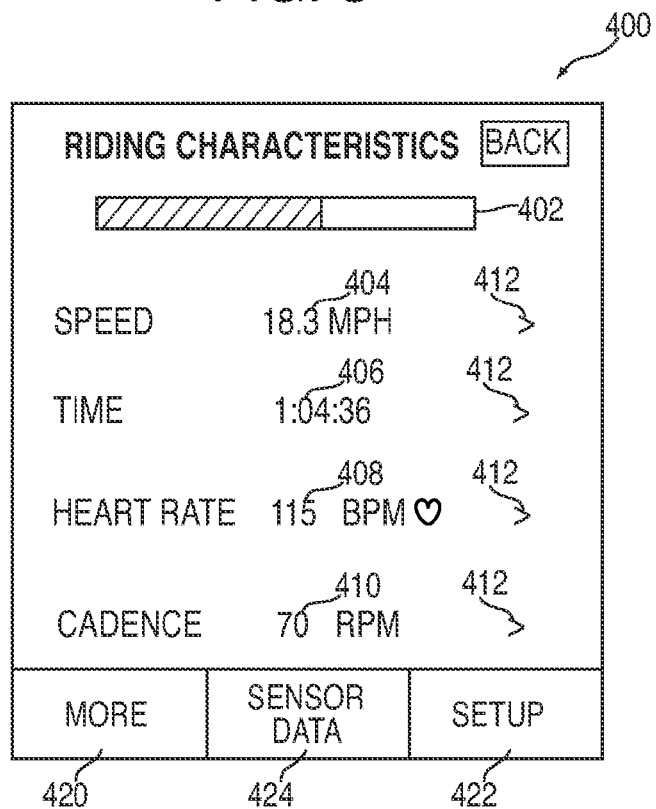
FIG. 4 is a schematic view of riding characteristics displayed to a user in accordance with one embodiment of the invention.

The user can direct the display to provide sensor data or riding characteristics determined from the sensors using any suitable approach, including for example in response to receiving a selection of Riding Characteristics option 302 (FIG. 3). In response to receiving a user selection of option 302, or any other instruction for accessing riding characteristics, the electronic device can display sensor data and riding characteristics, as determined in real-time by the sensors. FIG. 4 is a schematic view of riding characteristics displayed to a user in accordance with one embodiment of the invention. Display 400 can include information associated with one or more riding characteristics. For example, display 400 can include progress bar 402 indicating the distance run relative a predetermined target (e.g., a workout target or the length of the current course being ridden), speed 404, time 406, heart rate 408 and cadence 410. The user can view other riding characteristics using any suitable approach, including for example by selecting More option 420, and can view raw sensor data by selecting Sensor Data option 424. Alternatively, the user can access additional riding characteristics by scrolling the display.

The particular riding characteristics initially displayed can be selected using any suitable criteria, including for example as default riding characteristics (e.g., those of most interest to typical cyclists), based on the environment, or selected by the user. For example, the user can set which riding characteristics to display by selecting Setup option 422. In response to receiving a selection of setup option 422, the display can provide a listing of available riding characteristics or sensor data from which the user can select any suitable number of characteristics for display. In some embodiments, the user can also set up units (e.g., US or metric) for one or more riding characteristics (e.g., speed in US units, power in metric units).

Figure 5:
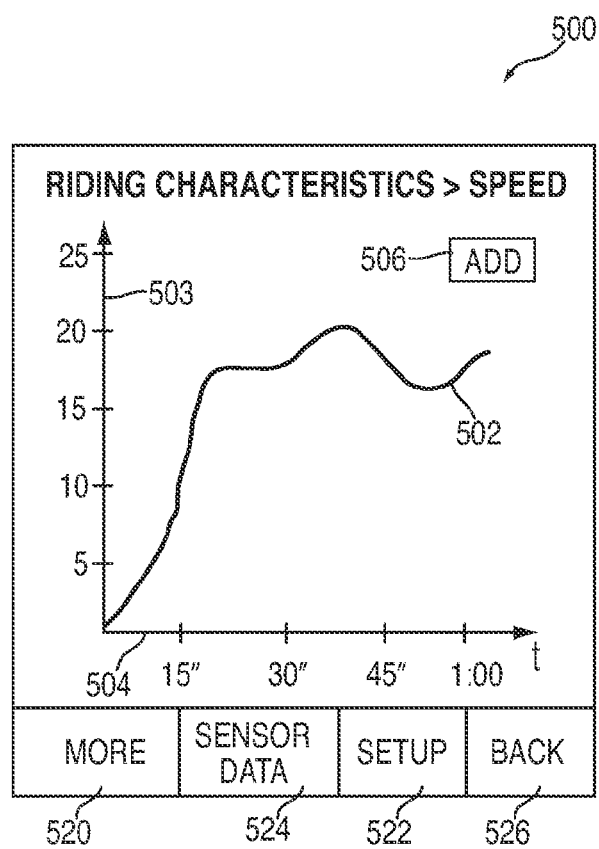
FIG. 5 is a schematic view of an illustrative display for viewing the evolution of a riding characteristic in accordance with one embodiment of the invention.

While the displayed riding characteristics can reflect the current values, a user can wish to view the evolution of one or more particular riding characteristics, or view a previous value (e.g., determine highest speed during a sprinting workout). In some embodiments, the electronic device can select arrow option 412 associated with any of the displayed riding characteristics to view an evolution of the riding characteristics. FIG. 5 is a schematic view of an illustrative display for viewing the evolution of a riding characteristic in accordance with one embodiment of the invention. Display 500 can include representation 502 of the evolution of the selected riding characteristic. Representation 502 can include any suitable representation, including for example a graphical representation (e.g., a line or bar graph). In the example of display 500, the evolution of speed along axis 503 is plotted along time axis 504. The user can add other riding characteristics to the representation using any suitable approach, including for example using Add option 506. In response to receiving a user selection of add option 506, the electronic device can display a listing of riding characteristics from which the user can select for display (e.g., on the same or a different representation).

The user can set up the displayed representation using any suitable approach. In some embodiments, the user can select Setup option 522 to set attributes of the display. For example, the user can set the color or appearance of the representation, the type of representation, units, the manner in which several riding characteristics are represented, or any other suitable attribute of the display. The user can access other riding characteristic information using More option 520, sensor data using Sensor Data option 524, and return to a previous display (e.g., display 400, FIG. 4) using Back option 526.

Because the electronic device can include communications circuitry, the user of the system can access, during the ride, remote databases of information of interest during the ride. For example, the communications circuitry can access a dedicated or cycling-specific database, or instead access a general remote source having information of interest (e.g., the Internet). Any suitable information not generated from sensors or components on the bicycle can be provided to the user. In some embodiments, the received information can further be tailored to the user based on the current location of the user, as determined by the positioning circuitry of the electronic device. For example, the electronic device can receive illustrative or sample routes starting at the user's current position, passing through the user's current position, or within a particular distance of the user's position. The electronic device can retrieve appropriate courses or routes from any suitable source. For example, the electronic device can access servers that include known routes available for cyclists. As another example, the electronic device can retrieve routes taken by other cyclists in the vicinity in the past, or currently being taken by other cyclists. The received routes can be displayed on a map, along with directions (e.g., turn-by-turn directions) for accessing or following a route. The user can select a route to ride using any suitable approach, including for example providing a selection input, or starting to ride a route.

In some embodiments, the received routes can be provided with additional information to enhance a user's ability to choose an appropriate route. For example, displayed routes can include photographs or other media (e.g., video or audio recordings) showing particular features of the route. The photographs or media can be associated with each route using any suitable approach, including for example taken from a library of photographs depicting the route (e.g., provided by the street view feature of Google Maps, provided by Google Inc. of Mountain View, Calif.), photographs or media recorded by cyclists having previously taken the route, or any other suitable source. The media can be tagged with location information to ensure that the proper media is associated with the displayed map. For example, media can be tagged using GPS or other universal coordinates, or as a particular distance from a starting point of the path.

In some embodiments, proposed routes can be tagged with information reflecting other cyclists' experience with the routes. For example, the electronic device can receive an indication of particular riders who have ridden each route (e.g., from tracking information provided by the electronic devices associated with other cyclists, or from information other cyclists uploaded to the remote source) and of the level or experience of those cyclists (e.g., as set by each cyclist or as determined by monitoring each cyclist's performance over time). The electronic device can in addition receive information related to the performance of other cyclists along proposed routes. For example, the electronic device can access and display information related to the times or speeds of other cyclists along a proposed path, calories burned, or any other information that provides the user with an indication of the difficulty or quality of one or more proposed rides.

In some embodiments, the electronic device can instead or in addition access reviews associated with one or more proposed rides. For example, other riders can provide reviews (e.g., 1 to 5 stars) for proposed rides, and provide an indication of their level or riding expectations to provide context for the reviews (e.g., an expert cyclist can give an easy ride a low review, while a beginning cyclist can give the same ride an excellent review). The reviews can include any suitable information, including for example one or more riding characteristics of the cyclists, road and weather conditions, traffic conditions, an indication of the danger of the ride (e.g., many cars, or sections prone to accidents), the difficulty of the ride (e.g., a long climb or a technically difficult mountain bike ride), elevation and incline information, and comments from difference cyclists (e.g., video, audio or written comments). The electronic device can instead or in addition identify variations to proposed paths (e.g., recommended detours) to make a ride easier or more challenging, or to view particular sights of interest.

Once a user has selected and is riding a course, the electronic device can automatically or in response to a user instruction record video, audio, or take photographs reflecting the course, and geo-tag the generated media for publishing. The electronic device can also prompt the user to provide a review of the course for publishing to the remote source to further expand the resources available to all cyclists. Publication can take place automatically, or in response to a particular instruction from the user.

Figure 6:
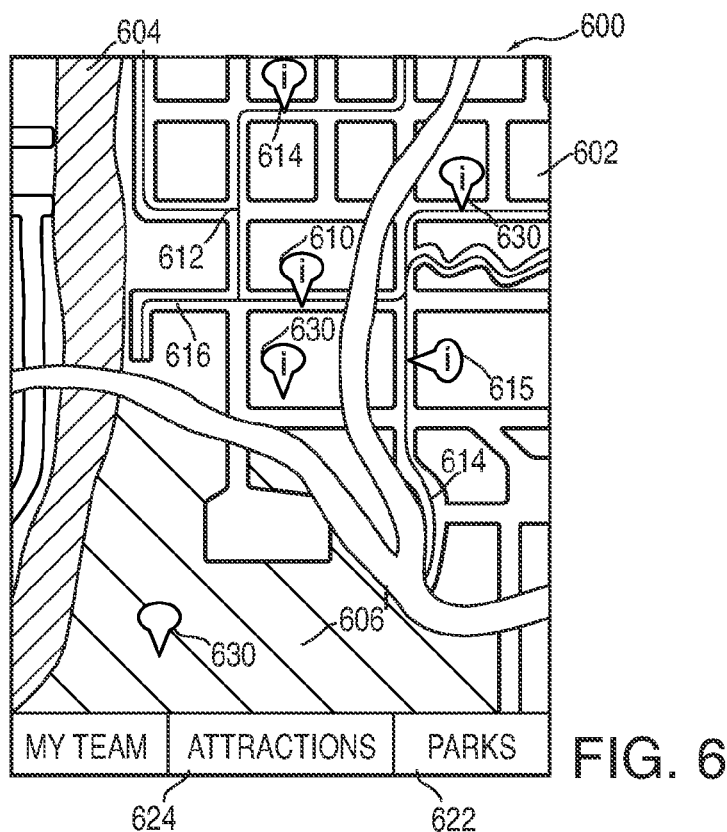
FIG. 6 is a schematic view of an illustrative display of a map in accordance with one embodiment of the invention.

FIG. 6 is a schematic view of an illustrative display of a map in accordance with one embodiment of the invention. Display 600 can include a map depicting at least one of the starting location, current location, and destination of the user. The user can access display 600 using any suitable approach, including for example in response to receiving a user selection of a Map option (e.g., Map option 304, FIG. 3). Display 600 can include map 602 depicting a region. The map can include a schematic representation, topological representation, photographic representation (e.g., satellite view), or any other suitable representation of a region. In the example of display 600, map 602 can include a road map with non-road regions, for example river 604 and park 606. The user's current position can be identified by marker 610, which can move in real time based on location information determined by the positioning circuitry of the electronic device. Display 600 can include path 612 depicting the path taken by the user up to the present, and the expected subsequent path to be followed by the user (e.g., if the user is riding along a known path).

Using the electronic device's communications circuitry, the user can direct the display to display additional information received from a remote source that can be of interest to the user. For example, display 600 can include one or more additional paths that the user can follow as he rides (e.g., paths 614 and 616). The displayed paths can be located near the user's current position, such that the user can easily move from his current path to one of the additional paths. A marker (e.g., markers 615 and 617, respectively) can be displayed to identify each additional path, and can be selected to display information about each path (e.g., starting and end points, distance, elevation change, difficulty, photographs, or reviews). The user can direct display 600 to provide additional paths using any suitable approach, including for example by selecting Path option 622.

In addition to displaying path information, display 600 can include photographs of the map location and identify local attractions that can be of interest to the user. For example, display 600 can include one or more markers 630 identifying local attractions and photographs. Each marker can include identifying information providing an indication of the nature of the attraction (e.g., a number or color associated with a type of attraction, ordering attractions in order of popularity or relation to defined interest, or a preview of a photograph). In response to receiving a user selection of a marker, the electronic device can display, for example in a pop-up window or in a new display, information associated with the selected attraction. Suitable attractions can include, for example, restaurants, museums, landmarks, events, hotels, or any other suitable attraction that can be of interest to the user. In some embodiments, the user can provide criteria for attractions to display. For example, in response to receiving a user selection of an attractions option (e.g., Attractions option 624), the electronic device can provide the user with an opportunity to enter criteria (e.g., provide criteria in a search field using an input mechanism). To reduce the clutter on the display, the user can toggle markers 630, for example using Attractions option 624.

In some embodiments, because the electronic device can be used for several rides, the electronic device can monitor a cyclist's performance over time to generate a riding profile reflecting the abilities of the user. The riding profile can include any suitable information, including for example riding characteristics, sensor data, courses followed, or any other suitable information associated with one or more rides, or portions of rides (e.g., review data associated with inclines). By comparing a user's current performance with past performance, the electronic device can provide the user with feedback as to his progress, or lack thereof. The electronic device can also provide a workout guide or plan based on one or more riding characteristics. For example, the electronic device can define one or more riding characteristic values as goals or targets for a particular workout. As the user rides, the electronic device can provide instructions to ride in a manner that reaches or exceeds the set riding characteristic goals (e.g., ride at a particular cadence or speed, or accelerate by a particular amount for a set duration or a particular gear or derailleur setting).

The electronic device can also allow the user to compare his performance to other specific cyclists or groups of cyclists, or to illustrative riding characteristics reflecting a particular cycling skill level. The electronic device can acquire comparison profiles with which the user can compare his performance from any suitable source. Each comparison profile can include any suitable information that permits an objective or quantitative evaluation of the user's performance. For example, each comparison profile can include one or more riding characteristic values (or sensor output values), or sets of riding characteristics that vary over time. The riding characteristics can include pre-determined values, or values determined as a result of external factors (e.g., an algorithm providing cadence and power values based on environmental factors), such as location or type of course, incline and decline, weather conditions (e.g., temperature, wind, humidity and rain), time of day, length of ride, lapsed time since start of ride, or any other suitable factor. During a ride, the electronic device can provide feedback (e.g., via the display) indicating the current riding characteristic of the user and the target riding characteristic of the comparison profile. In some embodiments, the electronic device can indicate a measure of the user's performance compared to the comparison profile, for example as a percentage difference, or using a graphical representation (e.g., a progress bar).

The electronic device can determine which comparison profile or comparison profiles to use using any suitable approach. In some embodiments, the user can select a particular comparison profile (e.g., based on the skill level associated with a particular profile, or the comparison profile of a friend or acquaintance). Alternatively, the electronic device can instead or in addition automatically select a comparison profile for the user. The electronic device can use any suitable criteria for determining which comparison profile or comparison profiles to use for monitoring the user's performance. For example, the electronic device can identify a comparison profile reflecting a skill level or fitness level that is higher (e.g., by a small or substantial amount) than that of the user, so that the user's performance can improve. As another example, the electronic device can identify a comparison profile that is substantially identical to the skill or fitness level of the user (e.g., so that the user maintains his skill or fitness level).

Figure 7:
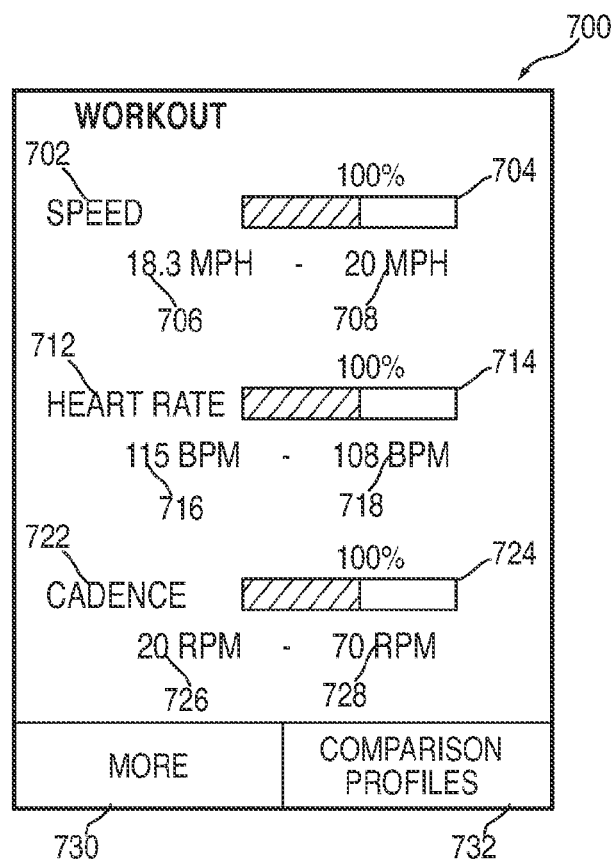
FIG. 7 is a schematic view of an illustrative display for comparing a user's riding characteristics to a workout goal in accordance with one embodiment of the invention.

FIG. 7 is a schematic view of an illustrative display for comparing a user's riding characteristics to a workout goal in accordance with one embodiment of the invention. The user can access display 700 using any suitable approach, including for example by selecting an appropriate on-screen option (e.g., option 306, FIG. 3). Display 700 can include one or more riding characteristics that are displayed and compared to target riding characteristic values (e.g., from a selected comparison profile). For example, display 700 can include speed 702, heart rate 712, and cadence 722. The display can include a graphical representation of the user's progress relative the target values, for example a progress bar (e.g., progress bars 704, 714 and 724, respectively). In some embodiments, display 700 can include a representation of the actual and target values associated with each of the riding characteristics. For example, display 700 can include actual speed 706 and target speed 708, actual heart rate 716 and target heart rate 718, and actual cadence 726 and target cadence 728.

The user can direct the display to provide information for other riding characteristics using any suitable approach, including for example by scrolling the displayed riding characteristics, selecting More option 730, or any other suitable approach. In addition, the user can select different comparison profiles or workout targets to match using any suitable approach. For example, the user can select Comparison Profiles option 732 to access a listing of available comparison profiles. The available comparison profiles can include locally stored comparison profiles (e.g., comparison profiles downloaded wirelessly or received from a host device during a synching operation) and comparison profiles available for download (e.g., available for purchase from a remote server). The listing of available comparison profiles can be organized in any suitable manner, including for example with recommended comparison profiles or comparison profiles most likely to be used displayed first, and other comparison profiles displayed after. In response to a user selection of a comparison profile, display 700 can replace the target riding characteristics with those of the selected comparison profile.

In some embodiments, the electronic device can direct the user to ride in a manner that reflects terrain or a course other than the user's current course. For example, the electronic device can direct a user to ride at a gear ratio and speed that reflects hills while the user is on flat ground. In particular, if the user's bicycle includes a mechanism for providing resistance (e.g., an electrical bicycle having a motor that can be charged by the user's pedaling), the resistance and riding characteristics selected by the electronic device can reflect a course other than the one on which the user is riding (e.g., reflect mountains instead of flat ground). This can allow a user to emulate riding any known ride (e.g., sample courses available from a remote source) at any suitable location (e.g., emulate riding the switchbacks of the Alpe d'Huez while in riding on Skyline boulevard in California).

To further enhance a user's cycling experience, the electronic device can be used to share riding characteristics or other information with one or more riders in a group riding with the user. In particular, the electronic device can communicate with other electronic devices or sensors associated with other cyclists of interest. Although the following discussion will generally use communications between electronic devices to illustrate this concept, it will be understood that it can also be used in the context of communications with or between sensors. The electronic device can identify other cyclists with whom to share information using any suitable approach. In some embodiments, the user can identify particular cyclists, or an electronic device identifier associated with electronic devices or sensors belonging to other cyclists. For example, the electronic device can select particular contacts from an address book with which the electronic device can be paired (e.g., use contact information from address book to identify and pair with selected contacts). As another example, the electronic device can identify other electronic devices associated with cyclists in the vicinity of the user, and provide a listing of cyclists from which the user can select (e.g., broadcast an identifier or detect broadcasted identifier). As still another example, the electronic device can receive a contact list from a remote source (e.g., the Internet) and pair with the devices associated with the downloaded contacts.

Figure 8:
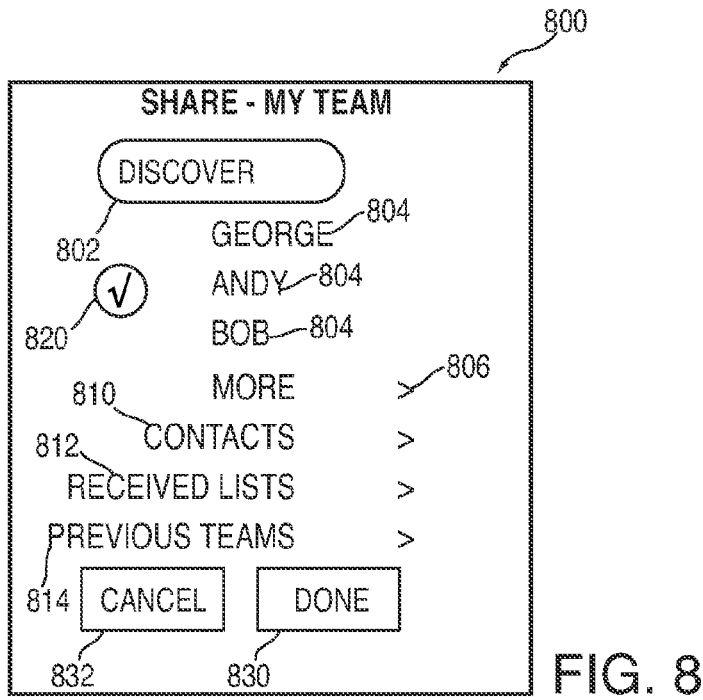
FIG. 8 is a schematic view of an illustrative display for selecting cyclists with which to share riding characteristics in accordance with one embodiment of the invention.

FIG. 8 is a schematic view of an illustrative display for selecting cyclists with which to share riding characteristics in accordance with one embodiment of the invention. The user can access display 800 using any suitable approach, including for example by selecting a Share option (e.g., Share option 308, FIG. 3). Display 800 can include several selectable options for selecting other cyclists to form a team with the user. For example, display 800 can include Discover option 802. In response to receiving a user selection of Discover option 802, the electronic device can monitor incoming communications for identifiers associated with other cyclists. Display 800 can then display identifiers 804 (e.g., in a new display or as sub-options) that were discovered by the electronic device from which the user can select to form a team. Identifiers 804 can include any suitable information identifying a particular cyclist, including for example a name associated with an electronic device or bicycle, an electronic device identifier, or any other suitable identifying information. Any suitable number of identifiers can be displayed, including for example identifiers having signal strengths higher than a particular threshold, a particular number of identifiers (e.g., 3), all detected identifiers, or any other suitable number. If the user knows of a particular cyclist that is not displayed (e.g., the received signal strength for that cyclist's identifier was lower than the threshold for display with identifiers 804), the user can provide an instruction to discover additional cyclists (e.g., More option 806). In some embodiments, display 800 can automatically display discovered identifiers, as discovery can be a preferred approach for selecting cyclists with which to ride.

Display 800 can include options associated with other approaches for selecting cyclists with which to share information. For example, display 800 can include Contacts option 810, Received Lists option 812 and Previous Teams option 814. In response to receiving a user selection of Contacts option 810, display 800 can provide a listing of known contacts, for example from an address book of the electronic device. The user can then select one or more contacts with which to share information. In response to receiving a user selection of the contacts, the electronic device can attempt to communicate with selected contacts, and if communication attempts are successful (e.g., the electronic devices of the user and the selected contacts are paired), the user and selected contacts can share riding characteristics. In some embodiments, the display can provide an indication of success or failure in pairing with selected contacts. Similarly, in response to receiving a user selection of Received Lists option 812, the electronic device can identify the contacts from a list received from a remote source (e.g., a race organizer) and attempt to pair with those contacts. In response to receiving a user selection of Previous Teams option 814, the electronic device can display previous groups of cyclists with whom the electronic device has communicated in the past, and attempt to pair with the cyclists of a selected one of those groups. Display 800 can indicate that a particular contact has been paired using any suitable approach, including for example using a visual indicator (e.g., icon 820) or an audio indicator (e.g., an audio tone). Once the user has selected all contacts with which to share riding characteristics, the user can select Done option 830, or Cancel option 832 to cancel the selections.

Figure 9:
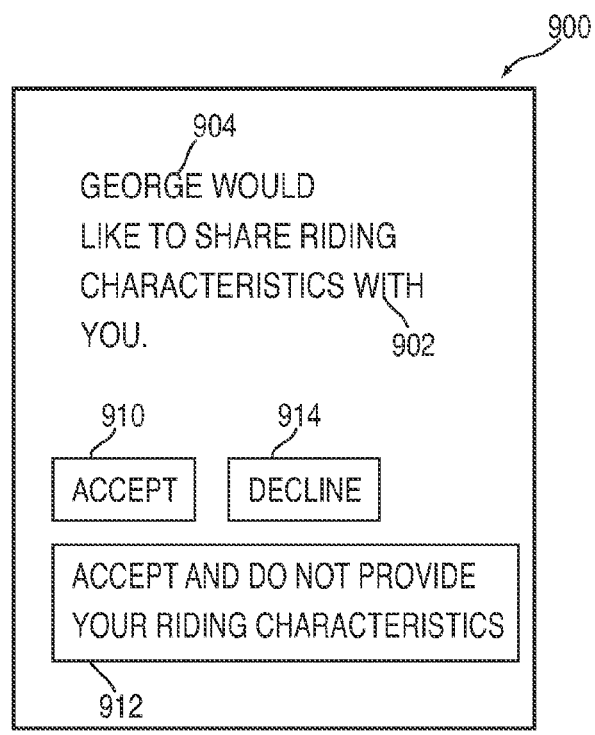
FIG. 9 is a schematic view of an illustrative display of a received sharing request in accordance with one embodiment of the invention.

In some embodiments, a user can receive requests from other cyclists to share riding characteristics. For example, the user can be selected by another cyclist using any of the approaches described above, and receive a pairing request from another electronic device. FIG. 9 is a schematic view of an illustrative display of a received sharing request in accordance with one embodiment of the invention. Display 900 can include indication 902 that one or more particular cyclists, for example identified by identifier 904, wish to share riding characteristics with the user. Display 900 can include several options for responding to the request, including for example Accept option 910 (and share you riding characteristics), Accept Without Sharing Your Riding Characteristics option 912, and Decline option 914. If several cyclists wish to share riding characteristics, display 900 can include several options 910, 912 and 914 associated with each of the identifiers, or the electronic device can provide different displays 900 for each identifier.

Once one or more other cyclists have been identified, the electronic device can automatically connect to the devices or sensors of the other cyclists, or only connect in response to a user instruction. For example, the electronic device can automatically connect to known or previously paired devices. If an unknown device is detected, the electronic device can prompt the user for an instruction to connect, or can instead or in addition automatically determine whether to connect based on attributes of the other electronic device. Such attributes can include, for example, the other cyclists with which the other electronic device is connected (e.g., is the other device connected with the other cyclists on the user's team), an authentication protocol (e.g., the other device has a proper key), the type of the other electronic device (e.g., is it a type that is exclusive to other cyclists of interest), or any other suitable characteristic. The electronic device can remain paired and communicate with other electronic devices for any suitable duration, including for example a fixed duration, the duration of the user's ride, while the other electronic devices remain in communication with the electronic device (e.g., the paired devices remain within the same communications network), until the user terminates or pauses the communications, until an other device terminates or pauses the communications, or any other suitable duration.

The electronic device can perform any suitable communications operation with other electronic devices with which it is communicating. In some embodiments, the electronic device can transmit or receive riding characteristics to or from other cyclists, for example in a group (e.g., a cycling team, or a peleton). Using the shared riding characteristic information, each cyclist in the group can adjust his efforts to match those of others in the group, for example to increase efforts when others are moving faster or to decrease efforts when others are moving slower (e.g., as determined from received cadence, speed, and gear ratio information). As another example, the group of cyclists can determine, from detected riding characteristics (e.g., power and calories burned), that one or more cyclists are fatiguing and protect those cyclists or reduce the efforts required by those cyclists by changing the group formation and allowing those cyclists to draft stronger cyclists within the group. As still another example, a group of cyclists (e.g., a team) can determine when particular cyclists can no longer follow the group and should fall back rather than continuing (e.g., during an attack). In effect, sharing such information among the cyclists themselves can allow a group of cyclists to themselves perform the duties that a cycling team manager, working from an automobile in the vicinity of the cyclists, would perform.

In some embodiments, riding characteristics can be shared among riders that are not necessarily team-mates or friends, but rather competitors. Receiving riding characteristics about a competitor can allow a cyclist to identify opportune moments for an attack, or moments when he might be subject to an attack, and to prepare tactically for such events. In some cases, a cyclist can intentionally ride in a manner that provides riding characteristics that do not reflect his actual physical condition (e.g., ride with a low power output or a low cadence) to create a tactical surprise on a competitor, for example in a race.

If the electronic device, sensors, or both are capable of performing long range communications operations, the electronic device can provide information to other cyclists at a significant distance from the cyclist's current position. Alternatively, the electronic device can relay riding characteristics to other devices trying to communicate while out of range (e.g., the electronic device can serve as a repeater). While transmitting many different riding characteristics can be of interest in long-range situations, transmitting position and speed information can be of particular interest. In particular, an electronic device can monitor the progress of other cyclists based on received position and speed information and infer, using known rides or paths (e.g., received from a remote source, as discussed above), future progress and locations of other cyclists. This can in turn allow the electronic device to determine a course and speed that the user can follow to intercept the other cyclists. To further assist the user in intercepting the other cyclists, the electronic device can recommend other riding characteristics to match, such as gear ratio (e.g., on a hill), cadence, when and where to take breaks, or any other riding characteristics. The electronic device can modify the recommended interception path and riding characteristics in real-time to reflect the progress or lack of progress of the user. In some embodiments, the user or other ridings can broadcast limited riding characteristics (e.g., only their locations) so that other cyclists or vehicles can be made aware of the cyclists' locations (e.g., to warn a car coming around a corner that there are cyclists ahead).

Figure 10:
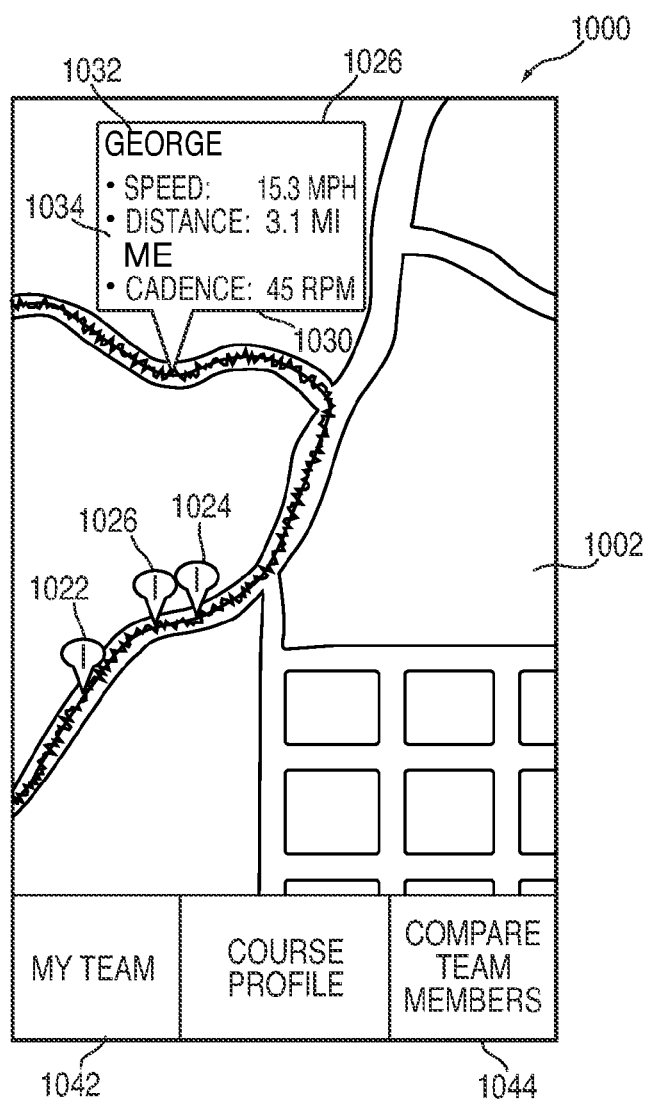
FIG. 10 is a schematic view of an illustrative display for viewing riding characteristics of particular cyclists in accordance with one embodiment of the invention.

FIG. 10 is a schematic view of an illustrative display for viewing riding characteristics of particular cyclists in accordance with one embodiment of the invention. The user can access display 1000 using any suitable approach, including for example by selecting a Share option (e.g., Share option 306, FIG. 3) or after selecting cyclists with which to share riding characteristics (e.g., as shown in display 800, FIG. 8 and display 900, FIG. 9). Display 1000 can include map 1002 depicting the environment near the user. Map 1002 can include any suitable type of map, including for example one or more of the map types described above in connection with display 600 (FIG. 6). Map 1002 can depict primary path 1012 followed by one or more of the cyclists with which the user is riding. For example, if all of the cyclists are riding together, path 1012 can depict the path of all of the cyclists. As another example, path 1012 can depict the path followed by a majority of the cyclists, or the path followed by at least the user. The location of each of the different cyclists riding with the user can be identified on map 1002 using markers. For example, map 1002 can include marker 1020 identifying the user's location, and markers 1022, 1024 and 1026 identifying the locations of different cyclists riding with the user. Each of markers 1022, 1024 and 1026 can be differentiated to allow the user to easily differentiate the markers (e.g., each marker includes a different number or color, or includes identifying information, such as the name of each cyclist). The user can select a marker to display additional information, such as riding characteristics, for the associated cyclist. For example, in response to selecting marker 1026, display 1000 can provide a window 1030 that includes identifier 1032 for identifying the particular cyclist, and riding characteristics 1034 detailing the status of the identified cyclist (e.g., speed, distance from the user and cadence). Window 1030 can include any suitable riding characteristic, or can be scrolled or paged to view additional riding characteristics. Using the provided riding characteristics, the user can determine whether the particular cyclist is falling behind or is catching up, or draw any other suitable conclusion as to the particular cyclist's performance.

In some embodiments, the riding characteristics provided in window 1030 can provide a limited view of a cyclist's performance. For example, a cyclist can be moving slowly because he is tired, or because he is going up a large hill. To enhance a user's ability to understand another cyclist's performance, the electronic device can display a course profile, for example in response to receiving a selection of Course Profile option 1040. The electronic device can also place markers for each of the cyclists riding with the user on the course profile to show each cyclist's progress along the course, and in particular along the more challenging or tiring portions of the course.

The user can call up riding characteristics for any particular cyclist using any suitable approach. In some embodiments, the user can select My Team option 1042 to view a listing of cyclists with whom the user is riding and select a particular cyclist from the listing to view his riding characteristics. The user can also compare the performance of different cyclists with each other or with him, for example using Compare option 1044.

While sharing riding characteristics can allow different cyclists in a group to monitor the performance of other cyclists, it requires each cyclist to individually review the received riding characteristics and make determinations as to the proper conduct to pursue. To further enhance each group's ability to ride together, the electronic device can allow cyclists within the group to transmit and receive communications and to communicate with other people outside of the cycling group (e.g., friends or family at home). Each electronic device can be operative to perform any suitable type of communications operation, including for example text or visual messages (e.g., e-mail and SMS communications), audio messages (e.g., telephone communications), and combinations of these (e.g., video conferencing). Using these communications mechanisms, different riders in a group can more easily coordinate cycling strategies, for example in a race or team context.

The electronic device can provide visual communications to the user using any suitable approach. In some embodiments, the electronic device can provide an indication of a received communication (e.g., a caller ID or a message header) to a display visible to the user (e.g., a display coupled to the user's handlebars or attached to the user's arm). The full communication (e.g., the e-mail or text message) can be displayed in response to receiving a user instruction (e.g., after displaying the initial indication), automatically after displaying the initial indication (e.g., after a predetermined delay, or when riding characteristics reach a particular level, for example indicative of less strenuous activity), when it is received (e.g., instead of displaying an initial indication), or at any other suitable time. If a message extends beyond the boundary of the display (e.g., the message is longer than the available display window), the electronic device can scroll the message automatically or in response to receive a particular user input.

Figure 11:
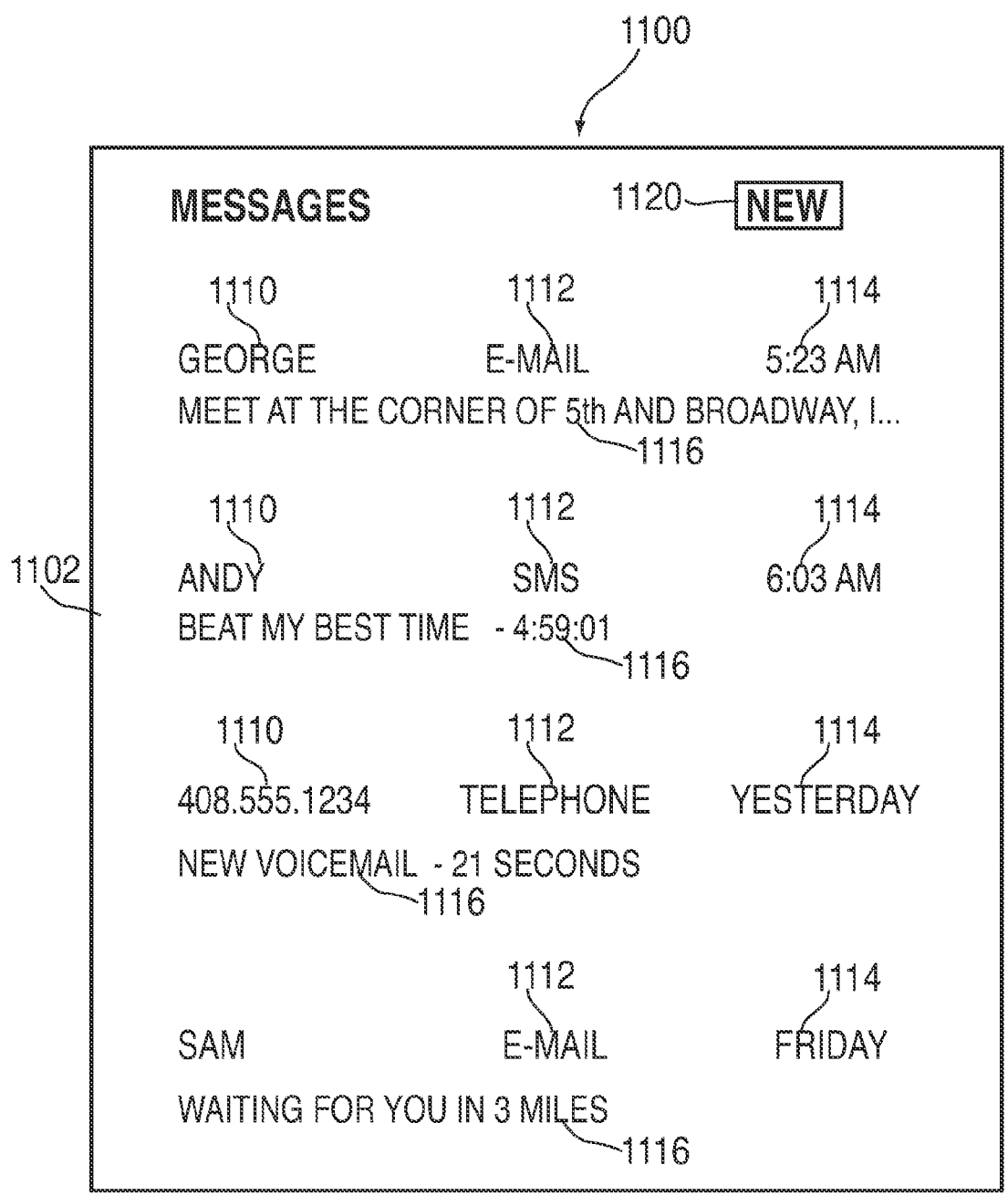
FIG. 11 is a schematic view of an illustrative display for generating and receiving communications in accordance with one embodiment of the invention.

FIG. 11 is a schematic view of an illustrative display for generating and receiving communications in accordance with one embodiment of the invention. Display 1100 can be displayed in response to any suitable user instruction, including for example a selection of a Messages option (e.g., Messages option 310, FIG. 3). In some embodiments, display 1100 can be automatically displayed, for example when a new message is received. Display 1100 can include listing 1102 of different types of messages received by the electronic device, for example from different cyclists with which the user is sharing information. Each listing can include identifier 1110 for identifying the person from whom the message was received, message type 1112 and time or date received 1114. When the message is visual (e.g., not audio), display 1110 can include message preview 1116 for viewing at least part of the message at a glance from display 1100. If the received message is non-visual, display 1100 can include message header 1116 providing information related to the non-visual message (e.g., the length of a new voicemail). The user can access a partially displayed message in its entirety, or access non-visual messages (e.g., voicemail) by selecting the listing associated with the message.

The user can direct the electronic device to generate and transmit visual communications (e.g., written messages) using any suitable approach. For example, the user can access a new message display by selecting a new message option, such as New option 1120. In some embodiments, the user can provide inputs reflecting particular letters or words to transmit (e.g., using a physical or virtual keyboard). Alternatively, the electronic device can provide one or more pre-generated messages that the user can select for transmission. The pre-generated messages can include generic messages, for example created as part of the electronic device firmware or software, or user created messages created prior to the ride (e.g., a message drafted on a host device and synchronized to the electronic device) or during previous rides (e.g., a message from a sent message).

The user can use any suitable input mechanism for selecting a message to send or for generating a new message (e.g., typing text or selecting media to transmit as part of the message). For example, the input mechanism can include one or more buttons on the electronic device, the display, the bicycle, the user's apparel (e.g., clothing or helmet), or another component that the user can actuate. As another example, the input mechanism can include a voice-actuated mechanism (e.g., voice selection of options, or a speech-to-text engine), a movement actuated mechanism (e.g., an accelerometer or other motion detection component), or any other input mechanism for providing hands-free inputs. In some embodiments, the electronic device can automatically send pre-selected messages when particular environmental conditions are met. For example, the electronic device can send a message to a friend or the user's home (e.g., the user's family) when the cyclist reaches a particular location (e.g., along a known path) or at a particular time (e.g., after a particular ride length), when a particular riding characteristic target is met (e.g., the number of calories burned reaches a target), or any other suitable condition is met.

The electronic device can perform audio communications using any suitable approach. In some embodiments, the electronic device can be coupled (e.g., wired or wirelessly) to an audio output mechanism located adjacent to or in the vicinity of the user's ear. To allow for two-way communications, a microphone coupled to the electronic device can be positioned adjacent to the user's mouth. Audio communications (e.g., telephone calls or radio communications) can be received and initiated using any suitable approach, including for example any of the approaches described above in connection with visual communications. This can in particular occur when an indication of an audio communication is provided on a display (e.g., a telephone caller ID is displayed), and the user provides an instruction to perform the audio communication (e.g., pick-up the telephone call). In some embodiments, the electronic device can convert received and transmitted audio in real-time (e.g., similar to closed-captioning) to provide a visual communication instead of an audio communication. This can provide a safer mechanism for communicating, as the user need not concentrate on received audio but can, at appropriate times, refer to a displayed transcript to perform the communications operation.

In some embodiments, the electronic device can include video conferencing capabilities. The electronic device, display, or another component on the bicycle can include a camera or lens for capturing real-time images of the user's face as he rides, and for transmitting the real-time images, accompanied with audio (e.g., if available), to other electronic devices. The other electronic devices can then display the received real-time images and play back the associated audio to provide both visual and audio communications. This approach can allow a cyclist to measure how other cyclists are riding from their appearance (e.g., how tired another cyclist's face looks) and sounds (e.g., the ease or difficulty of another cyclist's breathing). Video conferencing, or other communications that include both audio and video can be initialized or received using any of the approaches described above, for example in connection with visual communications.

Because the electronic device can communicate with both sensors embedded or coupled with a bicycle, and a remote server or source that can be accessed by other devices not necessarily related to cycling or the sensors (e.g., laptop or desktop computers), the electronic device can be used as an intermediary between sensors and the other devices. This intermediary position can, in some cases, be leveraged to provide security and theft protection for the bicycles associated with the sensors.

When an electronic device is initially used with a bicycle having one or more sensors, the electronic device can be paired with the sensors to ensure that they communicate properly together. If several electronic devices are used with the same bicycle and sensors, the sensors can be paired with each of the electronic devices. The one or more sensors can retain identifier information associated with each of the electronic devices, which can be used to determine whether electronic devices subsequently used in the vicinity of the bicycle were previously paired.

The one or more sensors can determine when a bicycle is in use. For example, a strain gauge can detect a displacement associated with riding the bicycle (e.g., detect a force applied to the pedals). As another example, a Hall effect sensor or a magnetic sensor can detect when the wheels are moving. In response to determining that the bicycle is moving, the one or more sensors can determine whether an authorized electronic device is in the vicinity of the sensors. For example, the sensors can compare identifiers received from electronic devices located in a communications network that includes the one or more sensors (e.g., broadcast identifiers, or identifiers provider in response to requests from the one or more sensors) with stored identifiers for previously paired devices. If no identifier is received (e.g., the bicycle is being used without an electronic device), the one or more sensors can provide an alert to a remote server or source. The alert can be tagged with location or position information, a time tag, a bicycle or sensor identifier, or any other metadata available to the one or more sensors and that could be of use in tracking the bicycle (e.g., current speed and direction). Similarly, if only identifiers for unauthorized electronic devices are detected, the one or more sensors can provide a STOLEN or UNSURE alert to the remote server.

The one or more sensors can provide a communication to a remote server using any suitable approach. In some embodiments, the one or more sensors can include communications circuitry suitable for transmitting the communication to the remote server (e.g., suitable long-range communications circuitry). In some embodiments, the one or more sensors can instead rely on communications circuitry of other devices located in communications range of the sensors (e.g., electronic devices in a short-range communications network used by the one or more sensors). In response to detecting another electronic device that has long-range communications circuitry, the one or more sensors can transmit an alert to the electronic device with instructions to forward to received alert to the remote server. In some embodiments, if a cyclist having an unauthorized electronic device uses the bicycle, the unauthorized electronic device can receive the alert from the one or more sensors and transmit the alert to the remote server.

Upon realizing that a bicycle was stolen, a user can access the remote server and receive the alerts generated by the one or more sensors. Using the sensor data provided in the alert, the user can track and recover a stolen bicycle. If the bicycle was in fact not stolen, but used with the owner's permission by a cyclist who did not own an appropriate electronic device, or if the owner himself rode the bicycle without an authorized electronic device, the owner can ignore the alerts provided to the remote server. In some embodiments, the owner can provide an indication to the remote server, for example by providing an input to the one or more sensors or by directly communicating with the server to ignore alerts received from the one or more sensors within given parameters (e.g., alerts received before a given date and time when the bicycle is to be returned, or alerts received from a region outside of a set home or authorized region). If the one or more sensors detect an authorized electronic device after having generated an alert, the sensors can generate and transmit a subsequent message canceling the previous alert.

Figure 12:
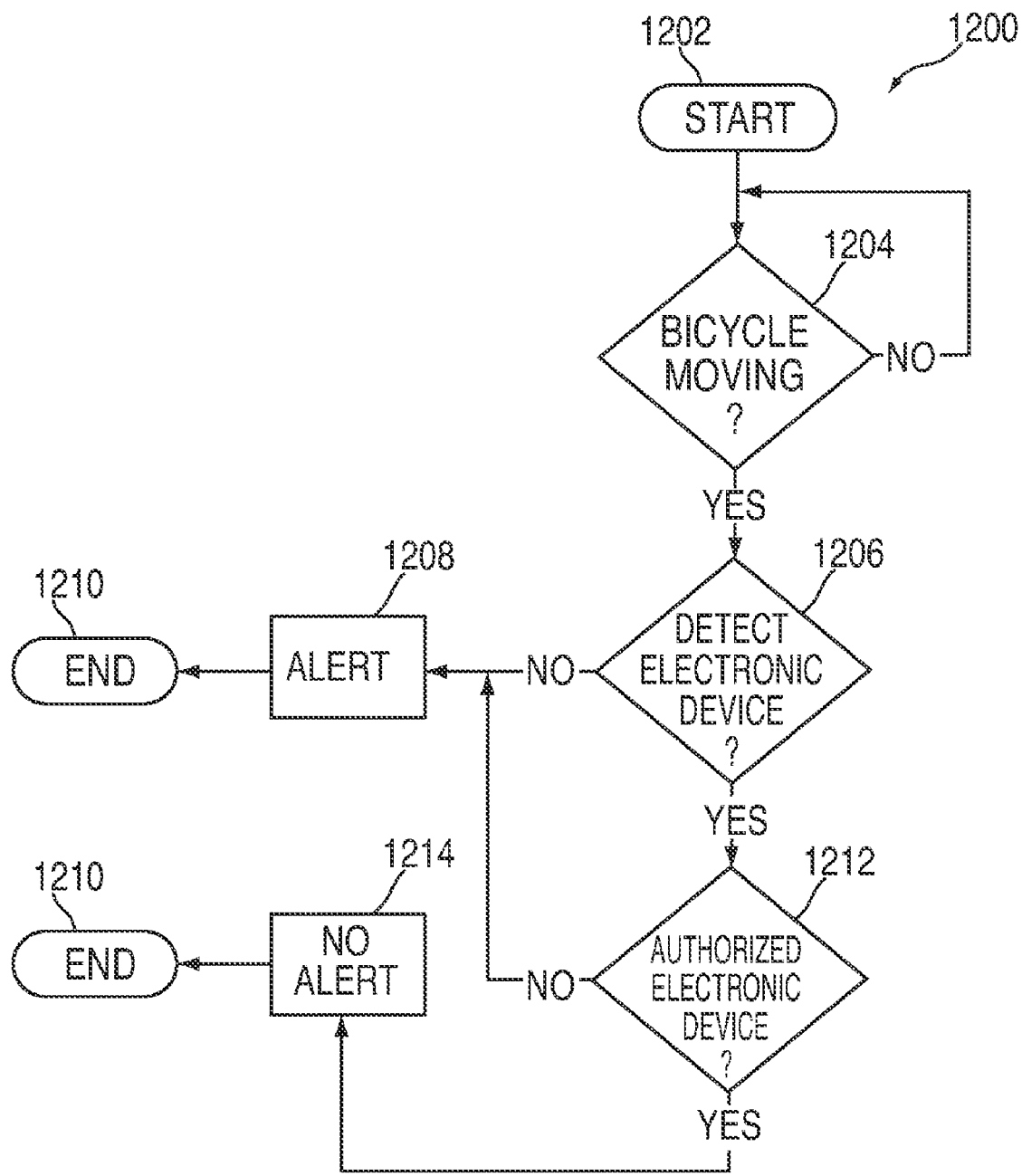
FIG. 12 is a flowchart of an illustrative process for determining whether a bicycle is moving unaccompanied by an authorized electronic device in accordance with one embodiment of the invention.

FIG. 12 is a flowchart of an illustrative process for determining whether a bicycle is moving unaccompanied by an authorized electronic device in accordance with one embodiment of the invention. Process 1200 can begin at step 1202. At step 1204, one or more sensors can determine whether the bicycle is moving (e.g., whether somebody is riding the bicycle). For example, the sensors can determine whether the sensor output reflects the movements associated with riding the bicycle (e.g., as opposed to the bicycle transported on a moving car). If the sensors determine that the bicycle is not moving, process 1200 can return to step 1204 and continue to monitor for movement of the bicycle.

If, at step 1204, the sensors instead determine that the bicycle is moving, process 1200 can move to step 1206. At step 1206, the sensors can determine whether an electronic device is detected. For example, the sensors can determine whether a communication from an electronic device was detected. The detected communication can include, for example, a pairing request or a broadcast of an identifier. If the sensors do not detect any electronic device, or the detected communications are not associated with somebody riding the bicycle (e.g., detecting intermittent communications from electronic devices of other cyclists in the vicinity), process 1200 can move to step 1208. At step 1208, the sensors can provide an alert. For example, the sensors can directly provide an alert to a remote server. As another example, the sensors can transmit a short-range alert to other electronic devices in the vicinity of the sensors for the other electronic devices to relay the alert to the remote sensor. The transmitted alert can include any suitable information, including for example location information and time information (e.g., time-stamped coordinates). Process 1200 can then end at step 1210.

If, at step 1206, the sensors instead detect a communication from an electronic device associated with the bicycle (e.g., an electronic device carried by the cyclist), process 1200 can move to step 1212. At step 1212, the sensors can determine whether the detected electronic device is authorized. For example, the sensors can determine whether the detected electronic device was previously paired with the sensors. As another example, the sensors can determine whether the detected electronic device is in a list of authorized devices (e.g., set as part of the sensor setup process). If the sensors determine that the electronic device is not an authorized electronic device, process 1200 can move to step 1208, described above. If the sensors instead determine that the detected electronic device is an authorized electronic device, process 1200 can move to step 1214 where no alert is provided, and end.

The above described embodiments of the invention are presented for purposes of illustration and not of limitation, and the present invention is limited only by the claims which follow.

What is claimed is:

1. An electronic device for providing cycling information of a plurality of bicycles that are riding in a group, the electronic device being associated with a first bicycle of the plurality of bicycles, the electronic device comprising control circuitry operative to:
   detect a plurality of other electronic devices, wherein each electronic device of the detected plurality of other electronic devices is associated with a respective bicycle of the plurality of bicycles;
   determine at least a first riding characteristic of at least one of the first bicycle and a first user that is riding the first bicycle;
   receive in real-time from at least one electronic device of the detected plurality of other electronic devices, at least a second riding characteristic of a second bicycle of the plurality of bicycles that is associated with the at least one electronic device and a second user that is riding the second bicycle;
   provide at least one riding recommendation of the first user based on at least the determined first riding characteristic and the received second riding characteristic;
   determine a current position of the first bicycle that is on a first cycling path;
   in response to the determining the current position, identify at least a second cycling path that is located in the vicinity of the determined current position; and
   provide the identified second cycling path to a display of the electronic device that is associated with the first bicycle for display to the first user.

2. The electronic device of claim 1, wherein the control circuitry is further operative to:
   receive an indication of an interest from the first user;
   in response to the receiving the indication, identify at least one attraction that is located in the vicinity of the determined current position and that is related to the interest; and
   provide the at least one identified attraction to the display to the first user.

3. The electronic device of claim 1, wherein the control circuitry provides the identified second cycling path to the display and the at least one identified attraction to the display by generating a map of the vicinity of the determined current position and displaying the generated map on the display, wherein the displayed map comprises representations of the identified second cycling path and the identified at least one attraction.

4. The electronic device of claim 1, wherein the control circuitry is further operative to:
   identify a location of the second bicycle that is associated with the at least one electronic device; and
   direct a display of the electronic device that is associated with the first bicycle to display the identified location and the received second riding characteristic.

5. The electronic device of claim 4, wherein the control circuitry is further operative to direct the display to display the identified location and the received second riding characteristic on a map that is displayed on the display.

6. The electronic device of claim 1, wherein the control circuitry is further operative to:
   receive a comparison profile comprising at least one particular riding characteristic; and
   direct a display to simultaneously display each of the at least one particular riding characteristic of the comparison profile and the determined first riding characteristic.

7. The electronic device of claim 6, wherein the control circuitry is further operative to:
   provide a listing of available comparison profiles, wherein at least one of the available comparison profiles corresponds to past riding performances of the first user of the first bicycle; and
   after the providing the listing, receive from the first user a selection of at least one of the available comparison profiles, wherein the received comparison profile is the at least one available comparison profile.

8. The electronic device of claim 6, wherein the comparison profile further comprises at least one riding characteristic that changes based on at least one of:
   an environment of the first bicycle,
   a location of the first bicycle along a course,
   a duration of a current ride of the first bicycle, and
   an amount of time that the first bicycle has been ridden.

9. The electronic device of claim 1, wherein the control circuitry is further operative to, prior to the receiving, receive from the first user a user selection of the second bicycle that is associated with the at least one electronic device of the plurality of other electronic devices from which to receive the second riding characteristic.

10. The electronic device of claim 1, wherein:
the first riding characteristic comprises a first performance metric of the first user;
the second riding characteristic comprises a second performance metric of the second user; and
the at least one riding recommendation comprises a recommendation for the first user to adjust a position of the first bicycle with respect to the second bicycle.

11. The electronic device of claim 10, wherein at least one of the first performance metric and the second performance metric comprises a physiological metric.

12. The electronic device of claim 11, wherein the physiological metric comprises at least one of a heart rate and calories burned.

13. The electronic device of claim 1, wherein:
the first riding characteristic comprises a first metric that is associated with the first bicycle;
the second riding characteristic comprises a second metric that is associated with the second bicycle; and
the at least one riding recommendation comprises a recommendation for the first user to adjust at least one of cadence, a speed of the first bicycle, and a gear ratio of the first bicycle.

14. The electronic device of claim 1, wherein the control circuitry is operative to provide the at least one riding recommendation to the first user by at least one of audibly announcing the at least one riding recommendation to the first user and displaying the at least one riding recommendation on a display of the electronic device that is associated with the first bicycle.

15. An electronic device that is operative to:
determine a first location of a first user;
determine a second location of a second user and a second speed of the second user;
predict a future location of the second user based on each of the determined second location, the determined second speed, and predefined path data; and
determine a path for the first user to reach the second user based on the determined first location and the predicted future location.

16. The electronic device of claim 15, wherein the predefined path data is received by the electronic device from a remote source.

17. The electronic device of claim 15, wherein the predefined path data is received by the electronic device from a remote source.

18. The electronic device of claim 15, wherein the electronic device is further operative to:
instruct the first user to follow the determined path;
determine a progress of the first user along the determined path; and
modify the determined path based on the determined progress.

19. The electronic device of claim 15, wherein the electronic device is further operative to:
determine at least one traveling characteristic to assist the first user in reaching the second user;
determine a progress of the first user along the determined path; and
modify the determined at least one characteristic based on the determined progress.

20. The electronic device of claim 15, wherein the electronic device is coupled to a first bicycle of the first user, and wherein the electronic device is operative to determine the second location and the second speed by receiving the second location and the second speed from another electronic device that is coupled to a second bicycle of the second user.

* * * * *